(12) United States Patent
Oikawa

(10) Patent No.: US 6,904,119 B2
(45) Date of Patent: Jun. 7, 2005

(54) RADIOGRAPHIC APPARATUS

(75) Inventor: Shiro Oikawa, Shiga-ken (JP)

(73) Assignee: Shimadzu Corporation, Kyoto (JP)

( * ) Notice: Subject to any disclaimer, the term of this patent is extended or adjusted under 35 U.S.C. 154(b) by 77 days.

(21) Appl. No.: 10/669,355

(22) Filed: Sep. 25, 2003

(65) Prior Publication Data

US 2004/0066880 A1 Apr. 8, 2004

(30) Foreign Application Priority Data

Oct. 2, 2002 (JP) .................................... 2002-289869
Oct. 20, 2002 (JP) .................................... 2002-289868

(51) Int. Cl.[7] .............................................. A61B 6/00
(52) U.S. Cl. .......................... 378/15; 378/197; 378/205
(58) Field of Search .............................. 378/4, 15, 21, 378/193, 196, 197, 205; 250/370.08, 370.09

(56) References Cited

U.S. PATENT DOCUMENTS

2002/0006185 A1 * 1/2002 Lienard et al. ............. 378/205

FOREIGN PATENT DOCUMENTS

JP   2001-045374 A1   2/2001

* cited by examiner

Primary Examiner—David V. Bruce
Assistant Examiner—Courtney Thomas
(74) Attorney, Agent, or Firm—Rader, Fishman & Grauer PLLC

(57) ABSTRACT

The radiographic apparatus according to this invention has a scan frame with an X-ray tube frame and a flat panel type detector (FPD) frame arranged therein. The X-ray tube frame surrounds an X-ray tube, and the FPD frame surrounds an FPD. The X-ray tube frame and FPD frame are rotatable together about a sectional axis. Thus, the X-ray tube and FPD rotate on the respective frames together directly about the sectional axis (for a main scan). Further, the X-ray tube and FPD are rotatable together about a scan center axis (for an auxiliary scan). The main scan and auxiliary scan are combined to achieve a high-speed scan and improves resolution in the direction of the sectional axis, thereby obtaining a three-dimensional sectional image with isotropic spatial resolution.

20 Claims, 15 Drawing Sheets

RADIOGRAPHIC APPARATUS

BACKGROUND OF THE INVENTION (1) Field of the Invention

This invention relates to radiographic apparatus for use in the medical field, and in industrial fields for performing non-destructive examinations, RI (Radio Isotope) examinations and optical examinations.

(2) Description of the Related Art

A conventional apparatus of this type includes a C-shaped arm supporting an X-ray tube at one end thereof and an image intensifier at the other end. The C arm is rotatable about the body axis of a patient or object under examination, i.e. the axis of a scan center shaft. The X-ray tube and image intensifier are thus rotatable together about the patient or object to scan it and obtain sectional images thereof (as disclosed in Japanese Unexamined Patent Publication 2001-45374 (page 3 and FIG. 1), for example).

However, the apparatus disclosed in the above patent publication has the following drawback. This drawback will be described with reference to FIG. 1. In FIG. 1, reference 101 denotes a C arm, 102 an X-ray tube, 103 an image intensifier, and M a patient. The C arm 101 is slid to rotate about the body axis (y-axis in FIG. 1) of patient M only through a range corresponding to the length of C arm 101. Since the movement of X-ray tube 102 and image intensifier 103 is limited to the range corresponding to the length of C arm 101, the C arm 101 cannot make one complete, continuous rotation about the axis of the scan center shaft (body axis). Thus, the X-ray tube 102 and image intensifier 103 are rotated about a sectional axis (z-axis in FIG. 1) in order to acquire sectional images of the entire patient M. This sectional axis is a different axis not parallel to the axis of the scan center shaft but extending through a site of interest of patient M. The X-ray tube 102 and image intensifier 103 are supported such that an X-ray beam center linking the X-ray tube 102 and image intensifier 103 is inclined at a predetermined angle α relative to the sectional axis (the angle α being called hereinafter "tomosynthetic angle"). The scan center axis and the sectional axis usually are set substantially perpendicular to each other.

The C arm 101 supporting the X-ray tube 102 and image intensifier 103 is required to have a sufficient length corresponding to an amount of sliding movement, and becomes heavy accordingly. In practice, therefore, the X-ray tube 102 and image intensifier 103 are not rotated directly about the sectional axis. The C arm 101 supporting the X-ray tube 102 and image intensifier 103 is rotated about the axis of an arm shaft (x-axis in FIG. 1), and the X-ray tube 102 and image intensifier 103 are rotated about the body axis of patient M (scan center axis). Thus, the X-ray tube 102 and image intensifier 103 are rotated indirectly about the sectional axis. This arm shaft is substantially perpendicular to the scan center shaft, and substantially perpendicular to the sectional axis.

(I)

Since the two shafts (scan center shaft and arm shaft) are rotated, it will take time (e.g. about six seconds) to rotate the X-ray tube 102 and image intensifier 103 about the sectional axis. Conversely, where the C arm 101, X-ray tube 102 and image intensifier 103 are arranged, respectively, to be rotatable directly about the sectional axis, the entire C arm 101 must be rotated about the sectional axis. Where the C arm 101 is rotated about the body axis of patient M (scan center axis), there is little chance of the C arm 101 colliding with the patient M. Where the entire C arm 101 is rotated about the sectional axis, the C arm 101 could collide with the end in the direction along the body axis, such as the head or feet, of patient M, and thus a rotating scan cannot be carried out safely.

(II)

Since the two shafts (scan center shaft and arm shaft) are rotated as noted above, the rotation of X-ray tube 102 and image intensifier 103 about the sectional axis results in an inconvenience that resolution along the sectional axis is lower than resolution along the other axes (e.g. the scan center axis). This is because the direction along the sectional axis corresponds only to a main scan in this invention, and low spatial resolution along the sectional axis results in anisotropic spatial resolution. Moreover, a high-speed scan is impossible because of the construction of the C arm.

On the other hand, a conventional X-ray CT apparatus has been developed to be capable of a continuous helical scan at a rate of about 0.5 sec. per rotation. However, this is still inadequate for imaging of a fast-acting internal organ such as the heart. A still image of the heart is reconstructed by combining ECG synchronous data collected from numerous angles during numerous rotations made for the same slice. Furthermore, it is impossible to realize isotropic spatial resolution because of the limitation of a simple helical scan.

SUMMARY OF THE INVENTION

This invention has been made having regard to the state of the art noted above, and its objects are to provide radiographic apparatus capable of (I) rotating a radiation source and a detecting device in a scanning operation safely and at high speed, and (II) besides the high-speed scan, obtaining a three-dimensional sectional image with isotropic spatial resolution by improving resolution along a sectional axis.

To fulfill the above object (I), Inventor has made intensive research and attained the following findings.

Inventor has directed his attention to the field of X-ray CT (Computed Tomography). In the field of CT, the concept of 4D CT (four-dimensional CT) has pervaded in recent years. This is an attempt not only to obtain a three-dimensional structure of an object under examination, but also to grasp variations with time thereof. Specifically, it has been studied as an attempt to obtain a dynamic sectional image of the heart. With a radiographic apparatus also, a dynamic sectional image of the heart is made possible by shortening a scan time taken in one rotation.

Generally, an X-ray CT apparatus is required to speed up a rotary frame which is a gantry having an X-ray tube and a detector. Since the radius of rotation of the X-ray tube and detector essentially cannot be reduced, the scan time in one rotation in the gantry is about 0.5 seconds and no reduction can be made thereof. In the case of a radiographic apparatus, on the other hand, the radius of rotation, about the sectional axis, of a radiation source such as an X-ray tube and a detecting device such as an image intensifier is smaller than the radius of rotation of the X-ray tube and detector in the CT gantry.

In the case of the X-ray CT apparatus, as shown in the side view of FIG. 2A, the X-ray tube and detector rotate about a sectional axis 202 of patient M within a gantry 201. In this case, the body axis of patient M runs parallel to the sectional axis 202. The tomosynthetic angle between the sectional axis 202 and the X-ray beam center linking the X-ray tube and detector is 90°. Inventor has formed a concept from X-ray CT that, as shown in the plan view of FIG. 2B, the tomosynthetic angle may be changed to an angle other than 90°, and a radiation source such as an X-ray tube and a detecting device may be rotated together about the sectional axis in a housing corresponding to the gantry. Then, the radius of rotation about the sectional axis of the radiation source and detecting device is reduced to require less torque. It is therefore possible to rotate the radiation source and detecting device at high speed.

Based on the above findings, this invention provides a radiographic apparatus comprising a radiation source for emitting an electromagnetic wave to an object under examination, a detecting device for detecting the electromagnetic wave emitted to and transmitted through the object, and a scan device for moving the radiation source and the detecting device together for scanning action, a three-dimensional sectional image being obtained from a group of projection data detected in varied positions of the detecting device moved by the scan device, wherein the radiation source and the detecting device are arranged such that a radiation axis linking the radiation source and the detecting device is inclined at a predetermined angle relative to a sectional axis passing through a site of interest of the object, and the scan device includes a radiation source housing for surrounding the radiation source, a detecting device housing for surrounding the detecting device, and a rotating device for rotating the radiation source and the detecting device in the respective housings together about the sectional axis.

According to this invention, the radiation source and detecting device are rotatable together about the sectional axis on the radiation source housing surrounding the radiation source and on the detecting device housing surrounding the detecting device, respectively. Thus, the radiation source and detecting device may be rotated safely for scanning action. The radiation source and detecting device are not rotated about an axis other than the sectional axis, as distinct from the prior art. The radiation source and detecting device may be rotated directly about the sectional axis, and therefore rotated safely and at high speed for scanning action.

For rotating the radiation source and detecting device in the respective housings about the sectional axis, the housings of the radiation source and detecting device may also be rotated about the sectional axis. Alternatively, the radiation source and detecting device may be rotated about the sectional axis, with the housings fixed.

Preferably, the radiation source housing and the detecting device housing are connected to a rotary shaft connected to the rotating device, the rotary shaft being disposed at an end of each of the housings. With this construction, the radiation source and detecting device may be rotated together on the respective housings about the sectional axis. The rotary shaft is disposed not adjacent the object under examination, but adjacent an end of each housing not to affect the object. Thus, the radiation source housing and detecting device housing connected through the rotary shaft may have a channel-shaped construction to give the object a feeling of openness.

The detecting device in this invention may, for example, be an image intensifier or a flat panel detector (hereinafter called "FPD" as appropriate). The flat panel detector has a plurality of gate lines switchable on and off for taking in the electromagnetic wave transmitted, and a plurality of read lines extending perpendicular to the gate lines for reading the projection data. Where the detecting device is the flat panel detector (FPD), the flat panel detector in one form is disposed such that each of the read lines extends along a projection axis formed by the sectional axis projected on a detecting plane of the FDP.

In the above form, it is preferred that the gate lines are turned on simultaneously to take in the electromagnetic wave in positions corresponding to the gate lines simultaneously as electric charges, the electric charges taken in being read as the projection data through the read lines, a lowpass filtering being effected on the projection data by turning on the gate lines simultaneously.

Since a lowpass filtering is effected on the projection data by turning on the gate lines simultaneously, artifacts appearing in a sectional image may be reduced by the low-pass filtering.

The scan device may be arranged such that the rotating device rotates the radiation source and the detecting device together to make one rotation about the sectional axis in 0.1 second at most. This enables a grasp of variations with time of a sectional image such as a dynamic sectional image of the heart, for example. By setting a small tomosynthetic angle between the sectional axis and the radiation axis linking the radiation source and detecting device, for example, the time taken for the radiation source and detecting device to make one rotation about the sectional axis may be shortened.

One example of the radiation source is an X-ray tube for emitting X rays. Thermoelectrons discharged from a cathode forming part of the X-ray tube are converted into X rays only at a low ratio by an anode forming part of the X-ray tube. The remaining thermoelectrons are converted into heat. In order to prevent damage by the heat generated at the anode, the X-ray tube often is a rotating anode X-ray tube including a cathode for discharging thermoelectrons, an anode for generating X rays upon collision with accelerated thermoelectrons from the cathode, and an anode rotating shaft for rotating the anode. However, the inertia of anode rotation in combination with the rotation of the radiation source and detecting device about the sectional axis could apply an excessive force to the anode rotating shaft, resulting in a burden on the X-ray tube. To avoid this inconvenience, the X-ray tube may be constructed and arranged so that the anode rotating shaft is parallel to the sectional axis. This reduces the force applied to the anode rotating shaft, thereby reducing the burden on the X-ray tube.

Apart from the above type, the X-ray tube may be a rotating cathode X-ray tube including a cathode for discharging thermoelectrons, an anode for generating X rays upon collision with accelerated thermoelectrons from the cathode, and a support for supporting the cathode. In this case, the anode may be shaped annular and fixed around an axis parallel to the sectional axis, the support being shaped annular around the axis parallel to the sectional axis, and the X-ray tube may be arranged so that the cathode is rotatable with the support about the axis parallel to the sectional axis. This reduces the force applied to the support and cathode due to a combination of the inertia of rotation of the support and cathode with the rotation of the radiation source and detecting device about the sectional axis, to reduce the burden on the X-ray tube.

Furthermore, to fulfill the above object (II), Inventor has made intensive research and attained the following findings.

In the case of an X-ray CT apparatus, as shown in the side view of FIG. 2A, the X-ray tube and detector rotate about the sectional axis 202 of patient M within the gantry 201. In this case, the body axis of patient M runs parallel to the sectional axis 202. The tomosynthetic angle between the sectional axis 202 and the X-ray beam center linking the X-ray tube and detector is 90°. Inventor has formed a concept from X-ray CT that, as shown in the plan view of FIG. 2B, the tomosynthetic angle may be changed to an angle other than 90°, and a radiation source such as an X-ray tube and a detecting device may be rotated together with a reduced radius of rotation about the sectional axis. It has been found that a main scan may be carried out at a high speed of 0.1 second per rotation, for example. It has been found also that a reconstructed image with isotropic spatial resolution may be obtained by adding an auxiliary scan for rotating the above main scanning structure about a patient or object under examination.

Based on the above findings, this invention provides a radiographic apparatus comprising a radiation source for emitting an electromagnetic wave to an object under examination, a detecting device for detecting the electromagnetic wave emitted to and transmitted through the object, a scan device for moving the radiation source and the detecting device together for scanning action, and an image processor for obtaining a three-dimensional sectional image from a group of projection data detected in varied positions of the detecting device moved by the scan device, wherein the radiation source and the detecting device are arranged such that a radiation axis linking the radiation source and the detecting device is inclined at a predetermined angle relative to a sectional axis passing through a site of interest of the object, and the scan device includes a main scan rotating device for rotating the radiation source and the detecting device together about the sectional axis, and an auxiliary scan rotating device for rotating the radiation source and the detecting device together relative to the object about a scan center axis which is one of axes extending substantially perpendicular to the sectional axis.

According to this invention, the main scan rotating device rotates the radiation source and the detecting device together about the sectional axis. Thus, the radiation source and the detecting device are not rotated about an axis other than the sectional axis, as distinct from the prior art. The radiation source and the detecting device may be rotated directly about the sectional axis. This realizes a high-speed main scan. Further, the auxiliary scan rotating device is provided for rotating the radiation source and the detecting device together relative to the object about the scan center axis which is one of axes perpendicular to the sectional axis. With the main scan added to the auxiliary scan, a three-dimensional sectional image with isotropic spatial resolution may be obtained.

The scan device may include a radiation source housing for surrounding the radiation source, and a detecting device housing for surrounding the detecting device, the main scan rotating device rotating the radiation source and the detecting device in the respective housings together about the sectional axis. The scan device may include a scan housing for surrounding the radiation source and the detecting device, the auxiliary scan rotating device rotating the radiation source and the detecting device in the scan housing together about the scan center axis. For rotating the radiation source and detecting device in the respective housings about the sectional axis, the housings of the radiation source and detecting device may also be rotated about the sectional axis. Alternatively, the radiation source and detecting device may be rotated about the sectional axis, with the housings fixed.

Preferably, the auxiliary scan rotating device includes a scan housing support member for holding the scan housing, and a feed mechanism between the scan housing support member and the scan housing for rotating the scan housing.

It is further preferred that the scan housing support member has an arcuate portion, the feed mechanism rotating the scan housing along an inner peripheral surface of the arcuate portion. The above feature allows the auxiliary scan rotating device to be simple in construction, and reduces a floor area for installing the whole radiographic apparatus.

The tomosynthetic angle to be described hereinafter is often set to 45° at most. Thus, when the radiation source and detecting device are inclined at the tomosynthetic angle relative to the sectional axis, a main scan rotation about the sectional axis is faster than an auxiliary scan rotation about the scan center axis.

A range of auxiliary scan rotation about the scan center axis may be set to at least $\pi-2\alpha$, where $\alpha$ is a tomosynthetic angle between the sectional axis and the radiation axis linking the radiation source and the detecting device. Then, a three-dimensional sectional image with isotropic spatial resolution may be obtained from the set range, without setting the range of auxiliary scan rotation about the scan center axis to $2\pi$ (one revolution) since the main scan rotation also takes place.

The scan center axis of the auxiliary scan and the sectional axis of the main scan are not limited to particular directions. In an ordinary radiographic apparatus, as in this invention, these axes are set horizontal or vertical.

For example, the scan center axis of the auxiliary scan may be a horizontal axis, and the sectional axis of the main scan a vertical axis. Alternatively, the scan center axis of the auxiliary scan may be a vertical axis, and the sectional axis of the main scan a horizontal axis.

In the latter case, the auxiliary scan rotating device may be arranged to rotate the radiation source and the detecting device together about the vertical axis relative to a ceiling surface. Alternatively, the auxiliary scan rotating device may be arranged to rotate the object about the vertical axis relative to a floor surface.

The scan device is arranged such that the main scan rotating device causes the radiation source and the detecting device to make one rotation about the sectional axis in at most 0.1 second. This enables a grasp of variations with time of a sectional image such as a dynamic sectional image of the heart, for example. By reducing the tomosynthetic angle between the sectional axis and the radiation axis linking the radiation source and the detecting device, for example, the time taken for the radiation source and the detecting device to make one rotation about the sectional axis may be shortened.

The scan device may be arranged such that the auxiliary scan rotating device causes the radiation source and the detecting device to make a half rotation about the scan center axis in at most 5 seconds. Where the object under examination is a patient, the patient can hold his or her breath or keep the body motionless for about 5 seconds or less. The radiation source and the detecting device may make a half rotation together about the scan center axis while the patient holds his or her breath or keep still. This results in a sectional image with little slippage.

This invention will particularly be described further with reference to FIGS. 17A and 17B. FIGS. 17A and 17B are explanatory views illustrating a three-dimensional sectional image collection with isotropic resolution from a heart region. FIG. 17A is a view showing a collected data distribution in Fourier space. FIG. 17B is a data collection timing chart. For expediency of description, the tomosynthetic angle $\alpha$ is assumed to be 15°. As shown in FIG. 17B, while the main scan is carried out with each one rotation of the radiation source and the detecting device taking 0.1 second (0.1 second per rotation), a slow auxiliary scan takes place through 150° (=180°−2×15°) about the scan center axis of the object for 5 seconds needed for a half rotation of the radiation source and the detecting device (10 seconds per rotation).

Preferably, the radiographic apparatus further comprises a measuring device for detecting biosignals from the object, and a radiation source control device for controlling the radiation source to emit the electromagnetic wave to the object synchronously with predetermined times in a periodic motion detected by the measuring device.

When a site to be imaged is in motion, projection data cannot be collected from the site in the same state. It is therefore difficult to reconstruct a good three-dimensional sectional image. Thus, the measuring device is provided for detecting the motion of the heart, thereby collecting projection data from the site in the same state efficiently without waste.

Data collection is performed in synchronism with the electrocardiographic (ECG) waveform as shown in FIG. 17B, in order to obtain a three-dimensional sectional image free from motion artifacts of the heart. As shown in hatched (oblique lines) portions in FIG. 17A, a Fourier space distribution of data obtained from one main scan rotation is a range of 30° (=2×α). It will be seen from FIGS. 17A and 17B that six main scan data collections may be carried out each corresponding to 30° of the auxiliary scan, to collect data for filling the entire Fourier space, i.e. to collect data for a three-dimensional sectional image with isotropic spatial resolution.

More particularly, as shown in the timing chart of FIG. 17B also, a transmitted X-ray image collection of the patient is performed during one main scan rotation, which is a continuous high-speed rotation, at a predetermined delay time after the a wave of ECG. This collecting operation is carried out a total of six times each synchronized to ECG of every 30°. In practice, the main scan rotation takes place continuously for five seconds of the auxiliary scan, instead of being limited to the times (0.1 second) represented by the black portions in FIG. 17B. The black portions represent times (0.1 second) when electromagnetic waves (X rays in this case) are emitted from the radiation source.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Preferred embodiments of this invention will be described in detail hereinafter with reference to the drawings.

The following first embodiment is a solution to the problem (I).

First Embodiment

Figure 1:
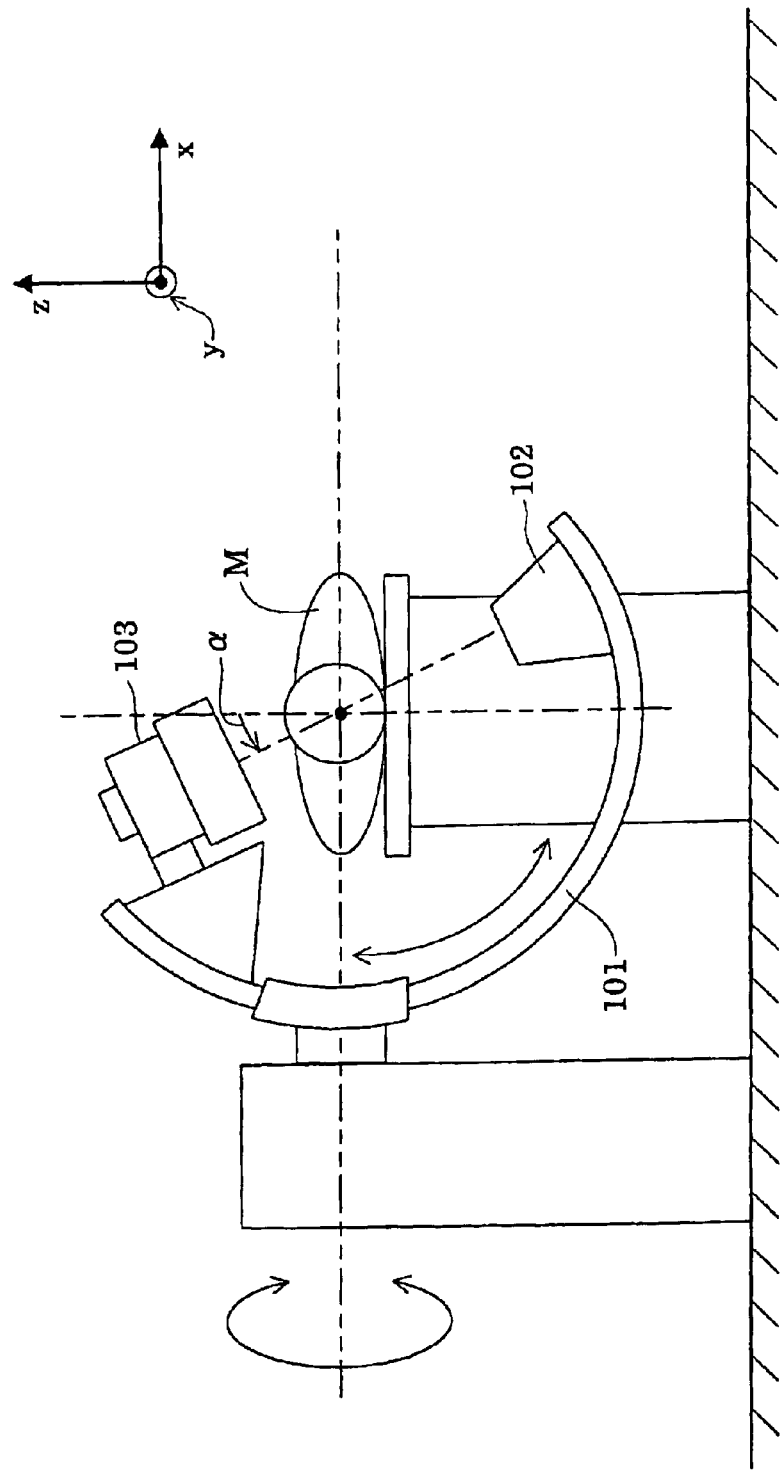
FIG. 1 is a schematic view of a conventional radiographic apparatus.
Figure 2:
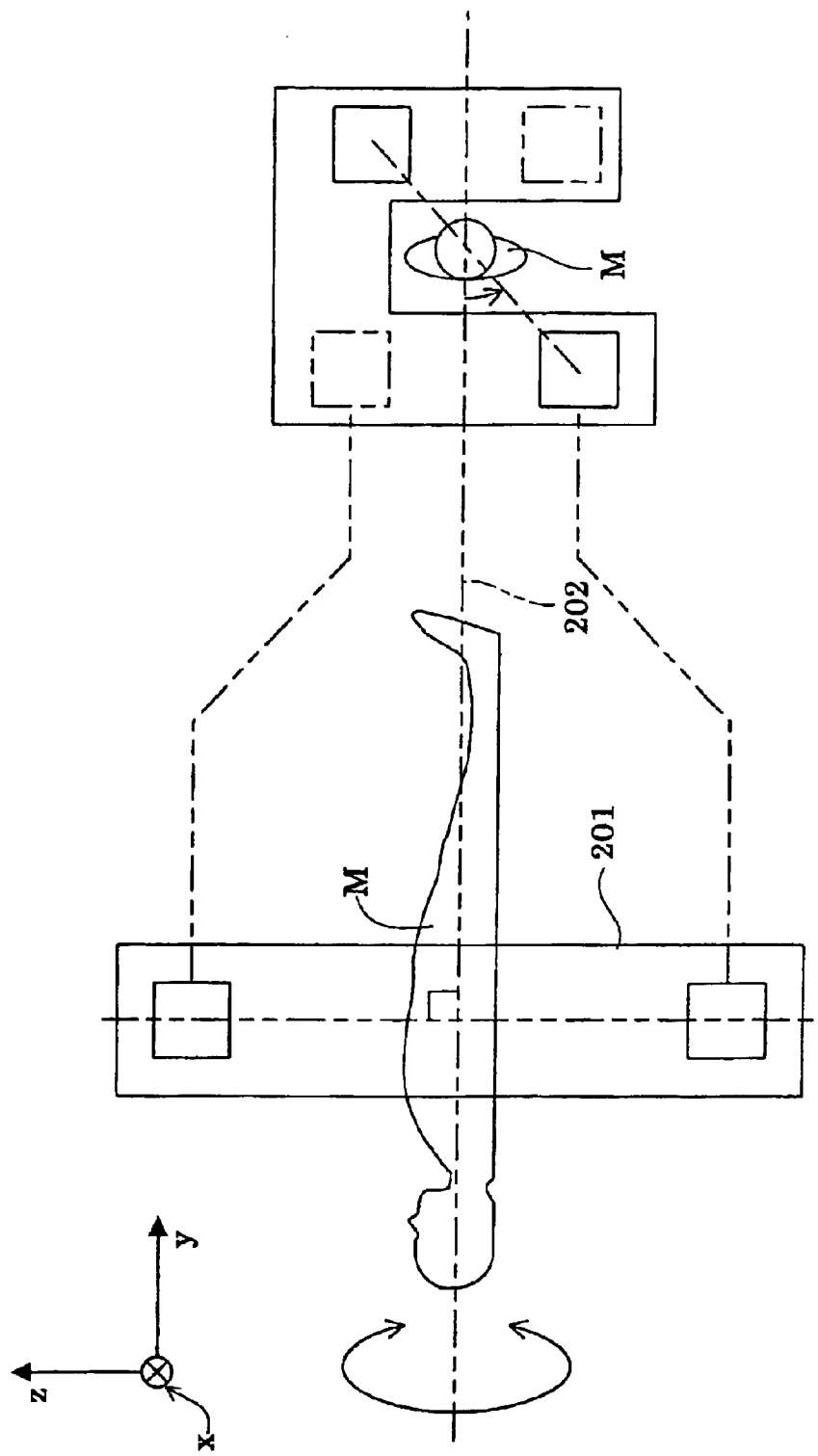
FIG. 2A is a schematic side view of an X-ray CT apparatus forming a basis for attaining findings leading to this invention.
FIG. 2B is a schematic front view of a radiographic apparatus forming a basis for attaining the findings leading to this invention.
Figure 3:
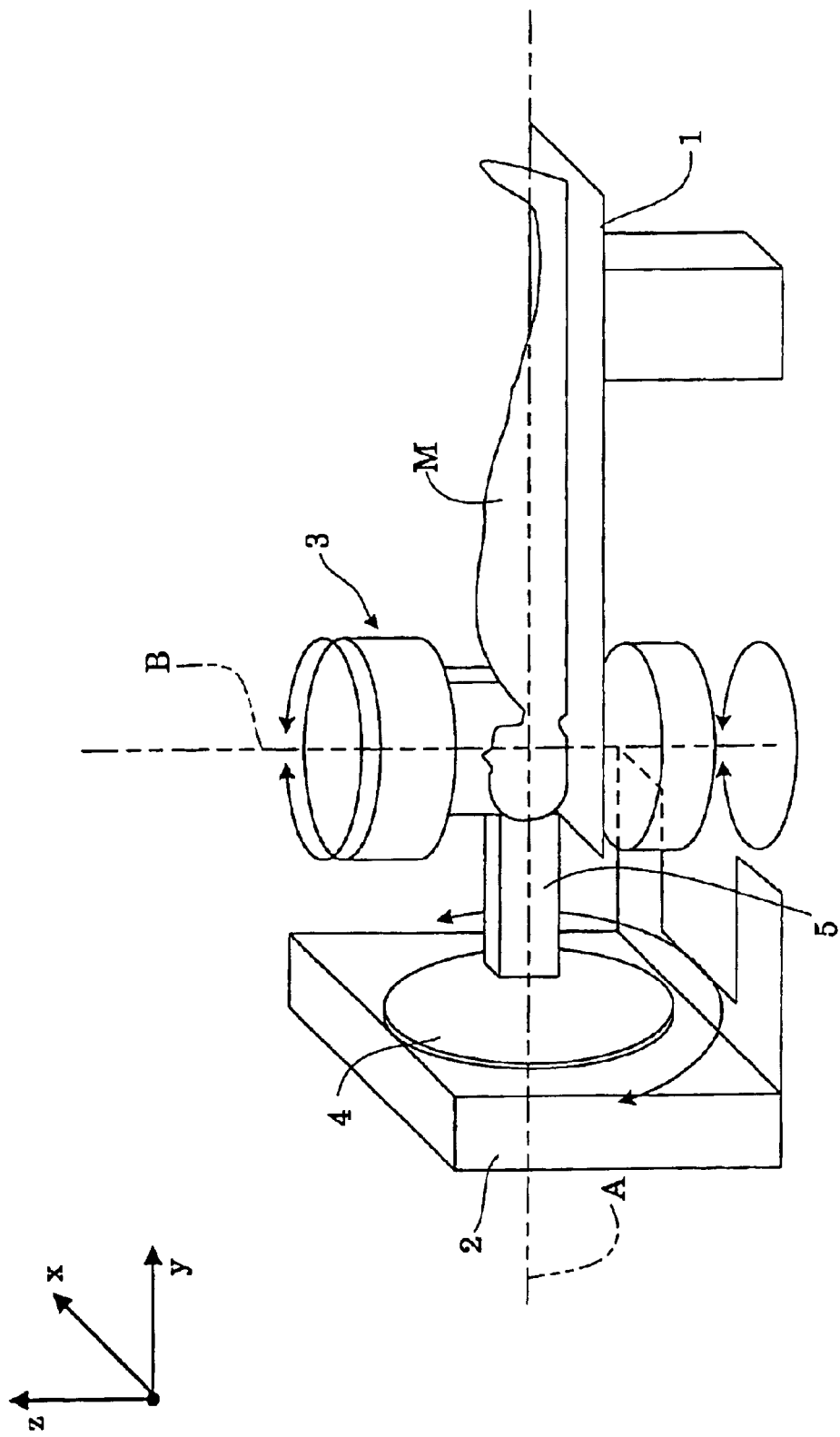
FIG. 3 is a perspective view showing an outline of a radiographic apparatus according to this invention.
Figure 4:
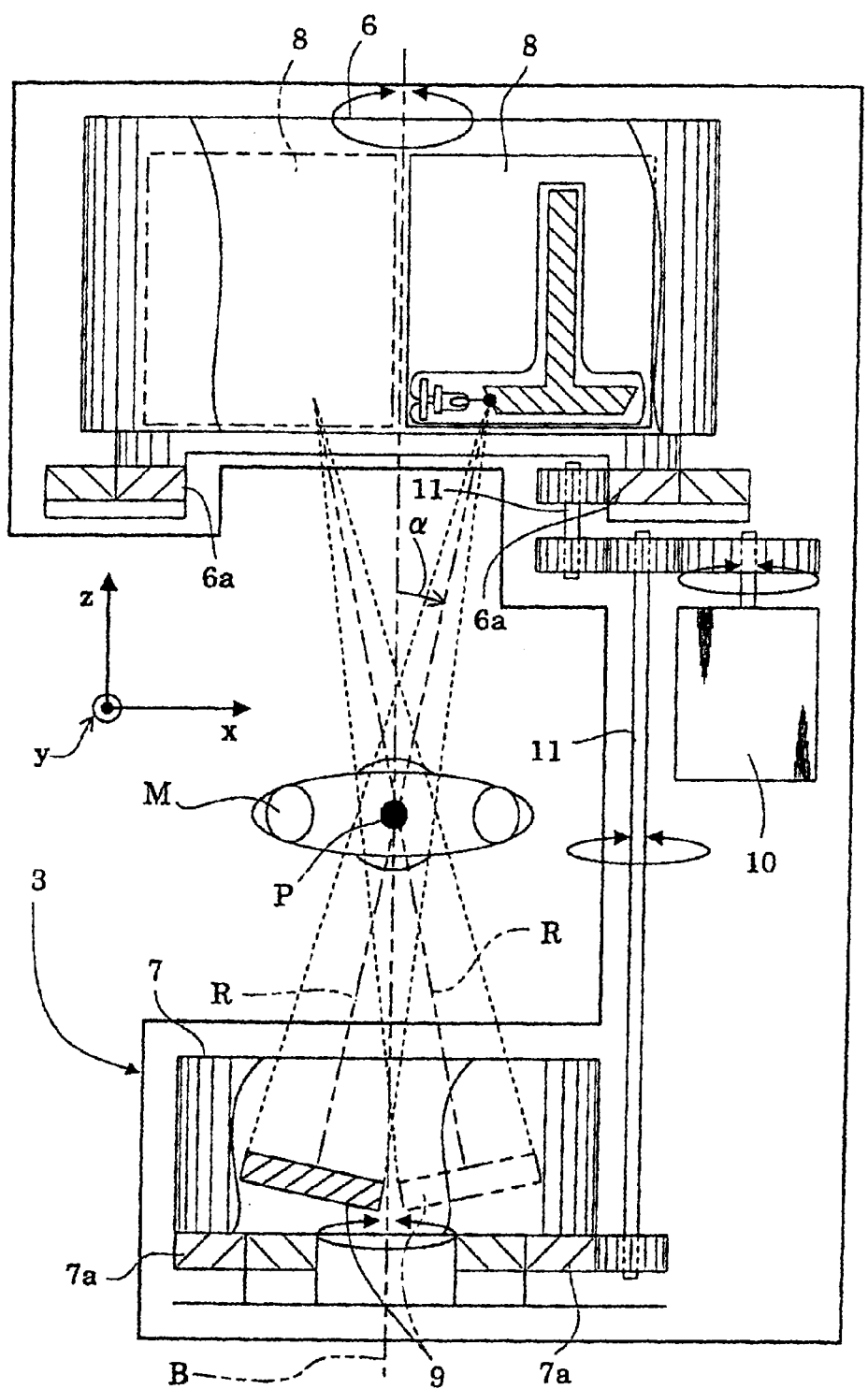
FIG. 4 is a right-hand side view of an X-ray tube frame and a flat panel detector (FPD) frame of the radiographic apparatus according to this invention.
Figure 5:
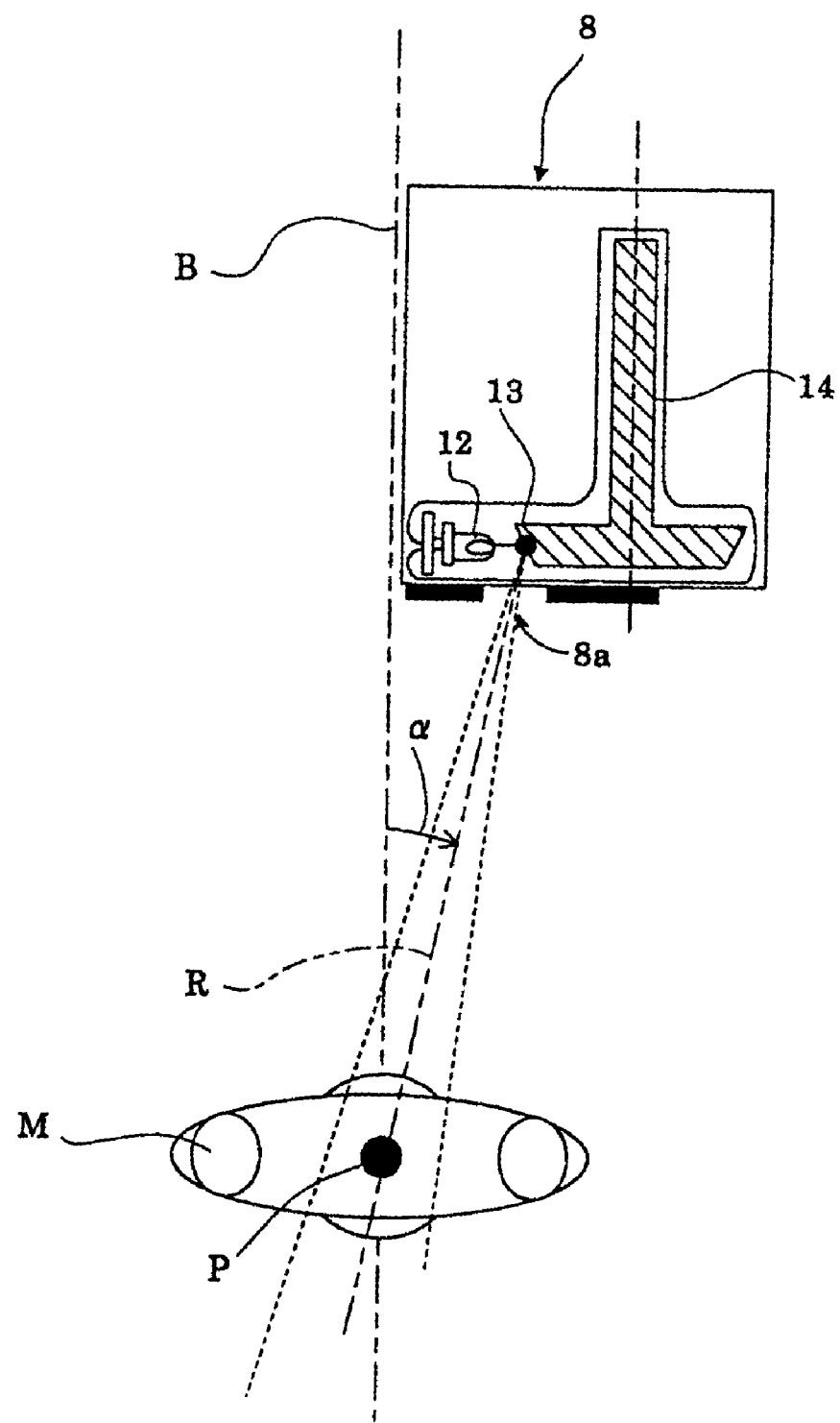
FIG. 5 is an enlarged view of an X-ray tube in the X-ray tube frame.
Figure 6:
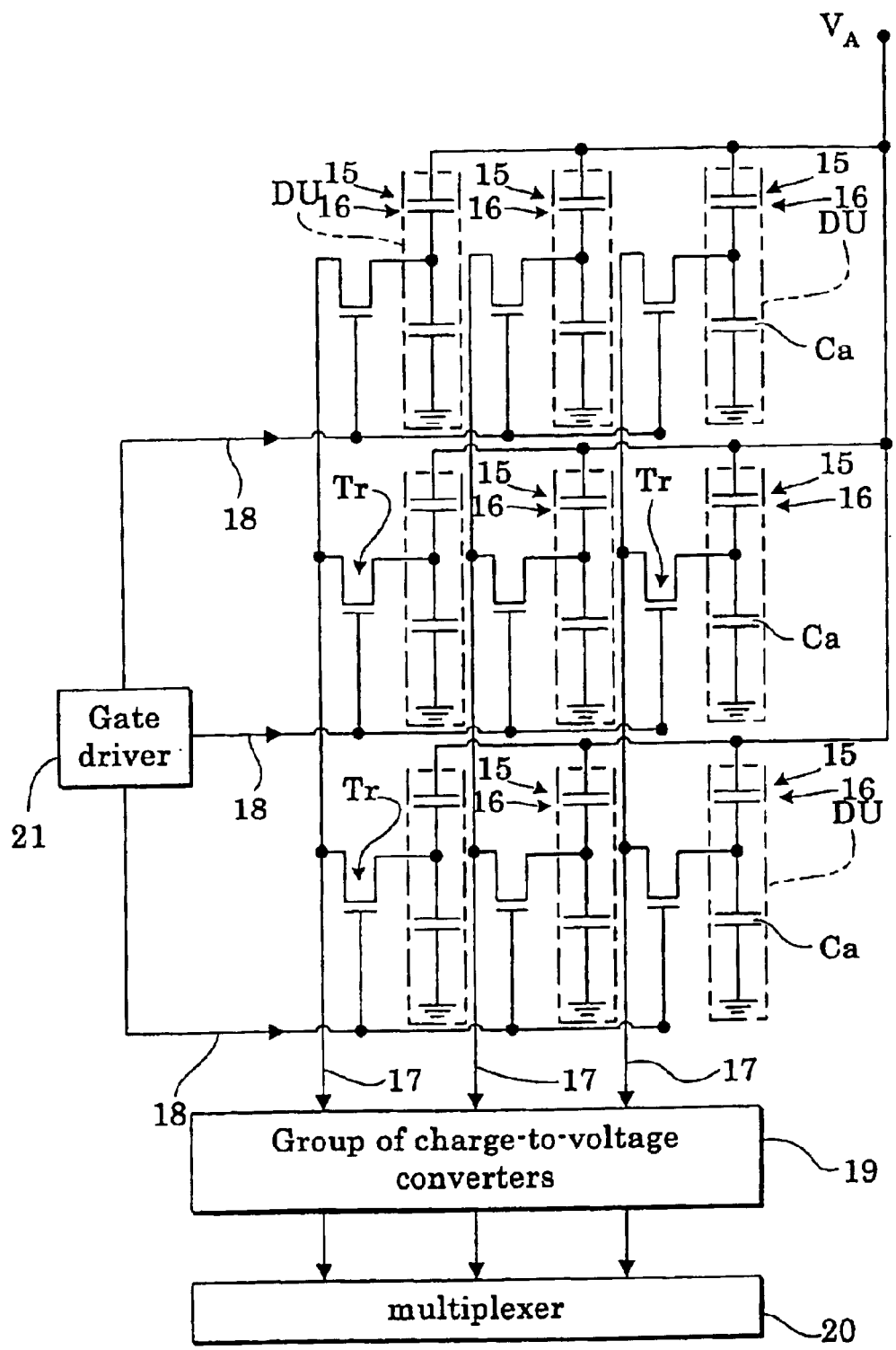
FIG. 6 is a block diagram of a flat panel detector (FPD) of the radiographic apparatus according to this invention.
Figure 7:
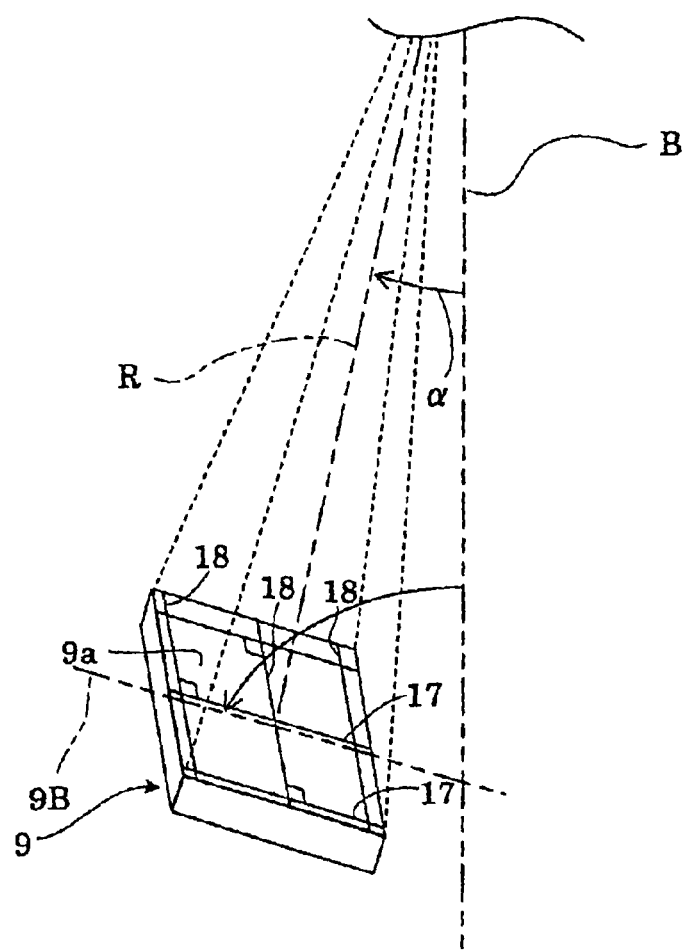
FIG. 7 is a perspective view of the flat panel detector (FPD) of FIG. 4 seen from an obliquely upper position, showing a relationship between gate lines and data lines forming the flat panel detector (FPD), and a sectional axis.

FIG. 3 is a perspective view showing an outline of a radiographic apparatus in this embodiment. FIG. 4 is a right-hand side view of an X-ray tube frame and a flat panel detector (hereinafter called "FPD" as appropriate) frame of the radiographic apparatus in this embodiment. FIG. 5 is an enlarged view of an X-ray tube in the X-ray tube frame. FIG. 6 is a block diagram of a flat panel detector (FPD) of the radiographic apparatus according to this embodiment. FIG. 7 is a perspective view of the flat panel detector (FPD) of FIG. 4 seen from an obliquely upper position, showing a relationship between gate lines and data lines forming the flat panel detector (FPD), and a sectional axis;

As shown in FIG. 3, the apparatus in this embodiment includes a top board 1 for supporting a patient M, a base 2 and a scan frame 3. The top board 1 is vertically movable and, as shown in FIG. 3, movable along the body axis of patient M (y-axis in FIGS. 3 and 4). The base 2 is fixedly mounted on a floor surface. The scan frame 3 is attached to the base 2 and fixed thereto except for rotation about the body axis of patient M. As shown in FIGS. 3 and 4, the scan frame 3 has a channel-shaped section. The channel-shaped construction gives the patient M a feeling of openness not obtained with an ordinary X-ray CT apparatus. In this embodiment, the body axis of patient M is a scan center axis A and is also a horizontal axis. The scan frame 3 corresponds to the scan device in this invention.

As shown in FIG. 3, the base 2 has a turntable 4 attached to a side surface thereof to be rotatable about the scan center axis (body axis). The turntable 4 and scan frame 3 are connected to each other through a support member 5. As shown in FIG. 4, the scan frame 3 has an X-ray tube frame 6 and a flat panel detector (FPD) frame 7 mounted therein. The X-ray tube frame 6 surrounds an X-ray tube 8, and the FPD frame 7 surrounds a flat panel detector (FPD) 9.

With this construction, the scan frame 3 is rotatable about the body axis of patient M, i.e. about the scan center axis. Further, the X-ray tube 8 and FPD 9 are rotatable about the sectional axis on the X-ray tube frame 6 and FPD frame 7 on the scan frame 3. The X-ray tube frame 6 corresponds to the radiation source housing in this invention. The FPD frame 7 corresponds to the detecting device housing in this invention. The X-ray tube 8 corresponds to the radiation source in this invention. The flat panel detector (FPD) 9 corresponds to the detecting device in this invention.

A specific construction of each of the frames 3, 6 and 7 will be described with reference to FIG. 4. The scan frame 3 has a rotary drive motor 10, rotary drive shafts 11, gears and bearings 6a and 7a mounted therein, besides the X-ray tube frame 6 and the FPD frame 7. The rotary drive motor 10 and rotary drive shafts 11 are connected to each other through gears. One rotary drive shaft 11 and X-ray tube frame 6 are connected to each other through a gear and the bearing 6a ring-shaped around an axis parallel to the sectional axis B (z-axis in FIGS. 3 and 4). The other rotary drive shaft 11 and FPD frame 7 are connected to each other through a gear and the bearing 7a ring-shaped around the axis parallel to the sectional axis B. The bearing 6a is joined with a surface of the X-ray tube frame 6, while the bearing 7a is joined with a surface of the FPD frame 7. Thus, the X-ray tube frame 6 and the FPD frame 7 are connected to the rotary drive shafts 11 connected to the rotary drive motor 10. In this embodiment, as shown in FIGS. 3 and 4, the sectional axis B extends vertically through a site of interest of patient M. The sectional axis B also extends perpendicular to the scan center axis A.

As shown in FIGS. 4 and 5, X rays are emitted from the X-ray tube 8 in a so-called "cone beam" shape with a predetermined angle of divergence. The X-ray tube 8 and FPD 9 are set so that, even when the X-ray tube 8 and FPD 9 are rotated about the sectional axis, the X-ray beam center R constantly extends through a substantially central position P of the site of interest of patient M. The X-ray tube 8 and FPD 9 are arranged so that the beam center R is inclined at a tomosynthetic angle α relative to the sectional axis B. In this embodiment, the tomosynthetic angle α is about 20°. The beam center R corresponds to the radiation axis in this invention.

With this construction, the respective frames 6 and 7 are rotatable about the sectional axis, and so are the X-ray tube 8 and FPD 9 together with the respective frames 6 and 7. The rotary drive motor 10 corresponds to the rotating device in this invention. The rotary drive shafts 11 correspond to the rotary shaft in this invention.

The apparatus in this embodiment employs a slip ring mechanism to prevent cables connected to the X-ray tube 8 and FPD 9 from becoming entangled when the frames 6 and 7 are rotated about the sectional axis B.

A specific construction of X-ray tube 8 will be described with reference to FIG. 5. The X-ray tube 8 employed in this embodiment is the rotating anode type shown in FIG. 5. Thus, the X-ray tube 8 includes a cathode (filament) 12 for discharging thermoelectrons, an anode 13 for generating X rays upon collision with accelerated thermoelectrons discharged from the cathode 12, and an anode rotating shaft 14 for rotating the anode 13. In practice, the thermoelectrons discharged from the cathode 12 are converted into X rays at the anode 13 only at a low ratio, the remainder being converted into heat. The anode rotating shaft 14 rotates the anode 13 in order to prevent damage by the heat generated at the anode 13.

The inertia of anode rotation in combination with the rotation of X-ray tube 8 and FPD 9 about the sectional axis could apply an excessive force to a holder portion of the anode rotating shaft 14, resulting in a burden on the X-ray tube 8. Thus, the X-ray tube 8 is constructed and arranged so that the anode rotating shaft 14 extends parallel to the sectional axis B, thereby reducing the force acting on the holder portion of the anode rotating shaft 14, and hence reducing the burden on the X-ray tube 8.

In this embodiment, X rays are generated and directed in a cone beam shape from the anode 13 of X-ray tube 8 in the direction shown in FIGS. 4 and 5. To set the anode rotating shaft 14 parallel to the sectional axis B, the X-ray tube 8 is constructed to have the cathode (filament) 12 disposed in the position shown in FIG. 5, and an X-ray radiating window 8a disposed in the position shown in FIG. 5.

As shown in FIGS. 4 and 5, the X rays generated from the anode 13 are emitted in the cone beam shape to the patient M. As shown in FIG. 4, the X rays are transmitted through the patient M to impinge upon the FPD 9. The beam center R is incident at the center of FPD 9, and opposite ends of the beam with the predetermined angle of divergence incident at the ends of FPD 9, respectively.

A specific construction of the flat panel detector (FPD) 9 will be described with reference to FIG. 6. The FPD 9 is a radiation sensitive detector for generating carriers in response to an incidence of radiation such as X rays. The FPD 9 is in the form of a two-dimensional matrix with numerous detecting elements DU arranged in a criss-cross pattern (e.g. 1,024×1,024). The detecting elements DU include charge storing capacitors Ca for storing carriers generated by the incidence of X rays transmitted through the patient M, an application electrode 15 for applying a high bias voltage VA, and carrier collecting electrodes 16 opposed to the application electrode 15 across a radiation sensitive semiconductor film (not shown). The detecting elements DU are formed separately from each other for the respective carrier collecting electrodes 16. The application electrode 15 is formed over an entire surface as a common electrode for all the detecting elements DU.

The FPD 9 further includes thin-film transistors (TFT) Tr acting as normally OFF (inoperative) switching elements for fetching the charges stored in the capacitors Ca, data lines (bit lines) 17 connected to the sources of the thin-film transistors Tr, and gate lines 18 connected to the gates of the thin-film transistors Tr. The data lines 17 are connected to a multiplexer 20 through a group of charge-to-voltage converters 19. The gate lines 18 are connected to a gate driver 21. The data lines 17 correspond to the read lines in this invention. The gate lines 18 correspond to the gate lines in this invention.

In this embodiment, as shown in FIG. 7, the FPD 9 is arranged so that each data line 17 extends along an projection axis 9B which is a projection of the sectional axis B on a detecting plane 9a of FPD 9. With this arrangement of FPD 9, each data line 17 constantly extends along the projection axis 9B formed by the sectional axis B projected on the detecting plane 9a of FPD 9 when the FPD 9 rotates about the sectional axis.

The gate driver 21 applies a voltage to a plurality of gate lines 18 to turn on the thin-film transistors Tr simultaneously. Then, X rays in the detecting elements DU corresponding to these gate lines 18 are simultaneously fetched as carriers. The fetched carriers are read as projection data through the data lines 17.

Specifically, the carriers generated by the incidence of X rays transmitted through the patient M are stored in the capacitors Ca. Since a plurality of gate lines 18 are turned on simultaneously, the carriers stored in the capacitors Ca in the detecting elements DU are simultaneously read to the data lines 17 through the thin-film transistors Tr. The carriers are converted to voltage data by the group of charge-to-voltage converters 19, and collected by the multiplexer 20 as projection data.

The projection data collected in this way is put to various image processes to obtain a three-dimensional sectional image. By turning on a plurality of gate lines 18 simultaneously, a lowpass filtering is carried out on the projection data read, thereby suppressing artifacts appearing in the sectional image.

According to the above radiographic apparatus in this embodiment, the X-ray tube 8 and FPD 9 are rotatable together about the sectional axis B on the X-ray tube frame 6 surrounding the X-ray tube 8 and on the FPD frame 7 surrounding the FPD 9. Thus, the X-ray tube 8 and FPD 9 may be rotated safely for scanning action. The X-ray tube 8 and FPD 9 are not rotated about an axis other than the sectional axis B, as distinct from the prior art. The X-ray tube 8 and FPD 9 may be rotated directly about the sectional axis, and therefore rotated safely and at high speed for scanning action.

In this embodiment, the X-ray tube frame 6 and FPD frame 7 are connected to the rotary drive shafts 11 connected to the rotary drive motor 10. It is therefore possible to rotate the X-ray tube 8 and FPD 9 about the sectional axis on the respective frames 6 and 7. The rotary drive shafts 11 are arranged at the ends of the respective frames 6 and 7 remote from the patient M not to affect the patient M. Thus, the frames 6 and 7 connected through the rotary drive shafts 11 may have the channel-shaped construction to give the patient M a feeling of openness.

The scan frame 3 is constructed so that the X-ray tube 8 and FPD 9 are driven by the rotary drive motor 10 to make one rotation about the sectional axis in 0.1 second or less. This enables a grasp of variations with time of a sectional image such as a dynamic sectional image of the heart, for example. By setting a small tomosynthetic angle α between the sectional axis B and the X-ray beam center R linking the X-ray tube 3 and FPD 9, for example, the time taken for the X-ray tube 8 and FPD 9 to make one rotation about the sectional axis may be shortened.

This invention is not limited to the foregoing embodiment, but may be modified as follows:

(1) The foregoing embodiment detects radiation, typically X rays, and obtains a sectional image from the radiation. The invention is not limited to radiation, but may employ any electromagnetic wave. For example, light may be detected to obtain a sectional image therefrom. In this case, the flat panel detector (FPD) is a light sensitive detector for generating carriers from incident light, and includes a light sensitive semiconductor film.

(2) In the foregoing embodiment, the X-ray tube frame 6 and FPD frame 7 are rotated about the sectional axis to rotate the X-ray tube 8 and FPD 9 about the sectional axis. As stated in the modification (7) described hereinafter, the X-ray tube frame 6 or a box-like X-ray tube 8 (FIG. 8) may be fixed, with a cathode and the like rotatable in the fixed box about the sectional axis.

(3) In the foregoing embodiment, the detecting device in this invention is a flat panel detector (FPD). The detecting device is not limited to a particular type as long as it detects an electromagnetic wave. The detecting device may be an image intensifier, for example. The detecting plane of the detecting device in this invention, represented by FPD 9 shown in FIG. 4, need not necessarily extend perpendicular to the X-ray beam center R, but may extend perpendicular to the sectional axis B.

(4) In the foregoing embodiment, the FPD 9 is arranged so that the data lines 17 corresponding to the read lines in this invention extend along the projection axis 9B which is a projection of the sectional axis B on the detecting plane 9a of FPD 9. This arrangement is not limitative where no lowpass filtering is carried out. For example, the FPD 9 may be arranged so that the gate lines 18 extend along the projection axis 9B (that is, the gate lines 18 extend perpendicular to the projection axis 9B), or may be arranged so that the data lines 17 cross the projection axis 9B obliquely. Further, where no lowpass filtering is carried out, a plurality of gate lines 18 corresponding to the gate lines in this invention need not be turned on simultaneously.

(5) In the foregoing embodiment, the X-ray tube frame 6 and FPD frame 7 are connected to the rotary drive shafts 11, corresponding to the rotary shaft in this invention, connected to the rotary drive motor 10 corresponding to the rotating device in this invention. Instead, the X-ray tube frame 6 and FPD frame 7 may be adapted rotatable independently of each other, but controlled to rotate synchronously together, about the sectional axis.

Figure 9:
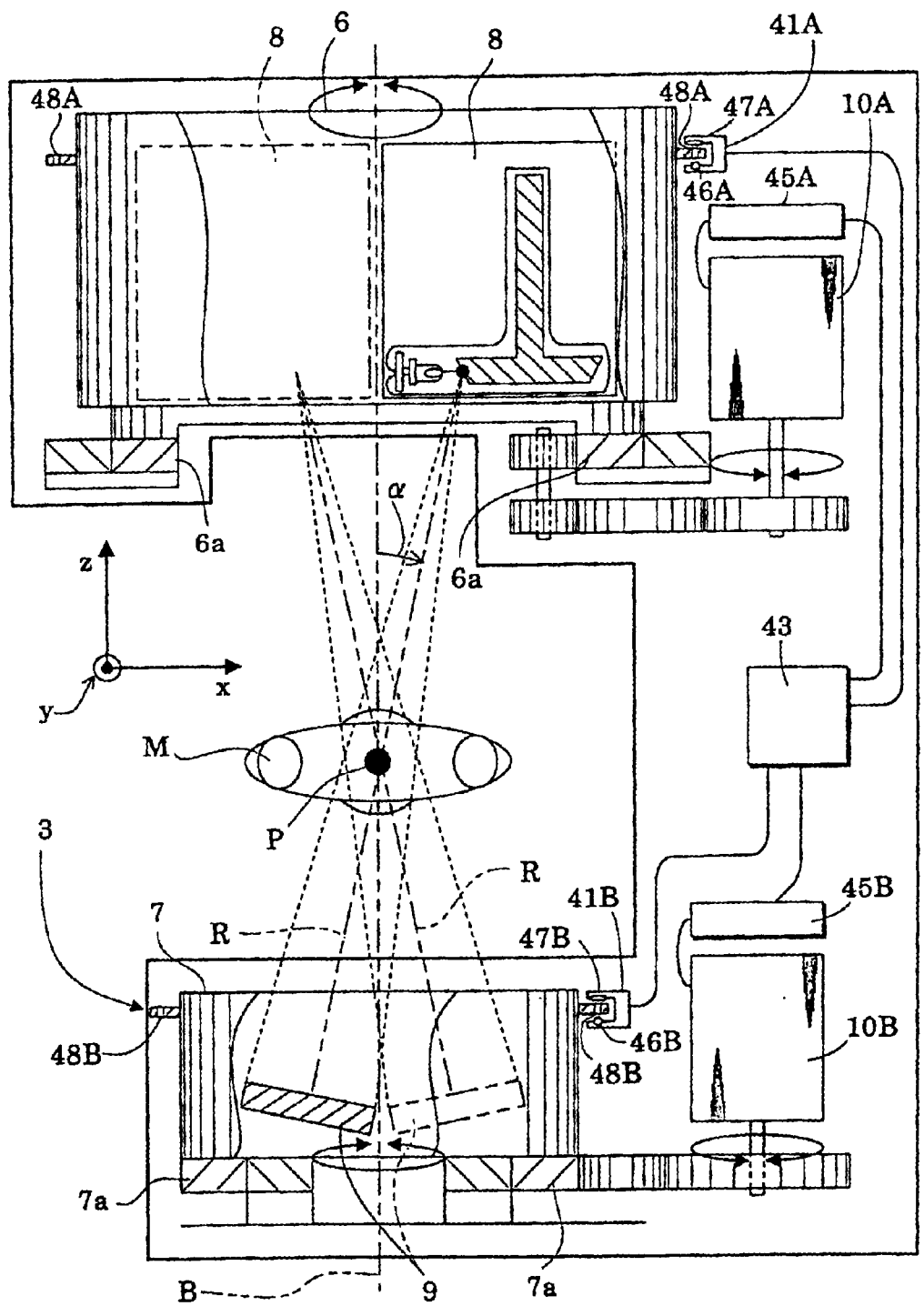
FIG. 9 is a right-hand side view of an X-ray tube frame and a flat panel detector (FPD) frame of a modified radiographic apparatus.

This modification will particularly be described with reference to FIG. 9. FIG. 9 is a right-hand side view of the X-ray tube frame and flat panel detector (FPD) frame of the modified radiographic apparatus.

The scan frame 3 houses an arithmetic unit 43, and separate rotary drive motors 10A and 10B, rotational position sensors 41A and 41B and rotation control units 45A and 45B for the X-ray tube and for the FPD.

The rotational position sensors 41A and 41B are installed laterally of the X-ray tube frame 6 and FPD frame 7. These sensors 41A and 41B detect rotational positions of the X-ray tube 8 and FPD 9, and transmit rotational position signals to the arithmetic unit 43. Each of the rotational position sensors 41A and 41B is, for example, an optical sensor including a light emitter 46A or 46B and a light receiver 47A or 47B forming a pair. The sensors 41A and 41B determine rotational positions of the frames 6 and 7 by detecting light passing through a plurality of optical slits 48A and 48B arranged circumferentially of the X-ray tube frame 6 and FPD frame 7, respectively.

The arithmetic unit 43 computes, from the rotational position signals, a phase difference between rotational positions of the X-ray tube 8 and FPD 9. Then, the arithmetic unit 43 transmits rotation control signals to the rotation control units 45A and 45B to eliminate the phase difference.

The rotation control units 45A and 45B control the rotary motors 10A and 10B based on the rotation control signals. In response to the rotation control signals, the rotary motors 10A and 10B rotate the X-ray tube frame 6 and FPD frame 7 through gears and bearings. A synchronized operation can be carried out by performing such a feedback control.

However, it is difficult to avoid a certain phase difference between rotational positions even with a feedback control. In this case, a reconstruction image with high resolution is realized by an inverse projection carried out in time of image reconstruction, reflecting a phase difference between rotational positions of X-ray tube 8 and FPD 9 obtained from the arithmetic unit 43. This is done for the following reasons. During a synchronized operation, the detecting plane 9a of FPD 9 is constantly in a position opposed to the X-ray tube 8 as shown in FIG. 9. X rays are detected in such a predetermined detecting position. When a phase difference occurs between the X-ray tube 8 and FPD 9, the detecting plane 9a detects X rays in a position displaced from the predetermined detecting position by an amount corresponding to the phase difference. A good sectional image cannot be obtained from an image reconstruction carried out on the assumption that X rays are detected in the predetermined detecting position although the detecting plane 9a is in fact displaced from the predetermined detecting position.

Thus, even with the X-ray tube frame 6 and FPD frame 7 adapted independently rotatable, a good sectional image can be obtained by performing a feedback control and a compensation for a phase difference.

Furthermore, this construction can dispense with the rotary drive shafts 11 connected to the X-ray tube frame 6 and FPD frame 7. It is thus possible to modify the scan frame 3 into an arcuate shape like the C arm, or to provide separate scan frames housing the X-ray tube frame 6 and the FPD frame 7. Consequently, the scan frame 3 may secure an enlarged space around the patient M.

The feature of this invention for causing the radiation source and detecting device to move together for scanning action, includes the above modification for rotating the X-ray tube frame 6 and FPD frame 7 independently and synchronously for scanning action.

(6) In the foregoing embodiment, the radiation source of this invention is the X-ray tube 8 which emits X rays. The invention is not limited to the above, but may employ a device for emitting any electromagnetic wave. For example, the radiation source may emit light.

(7) In the foregoing embodiment, the X-ray tube 8 is the rotating anode type. The X-ray tube 8 is constructed so that the anode rotating shaft 14 is parallel to the sectional axis B as shown in FIG. 5, to reduce the force acting on the holder portion of the anode rotating shaft 14 and to reduce the burden on the X-ray tube 8. The type of X-ray tube is not limited to the foregoing embodiment.

Figure 8:
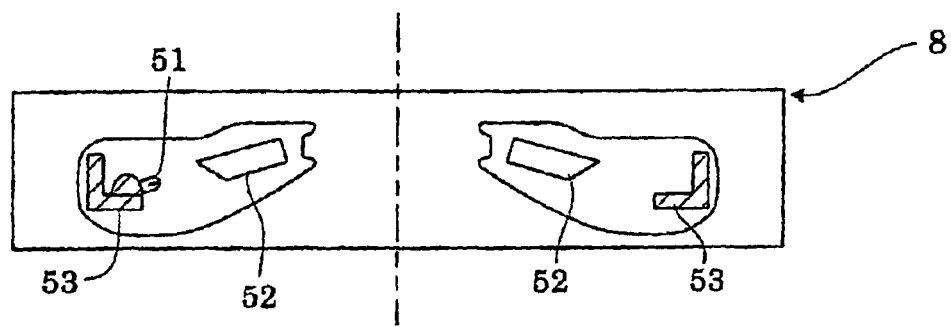
FIG. 8 is a schematic view of a modified X-ray tube.

The X-ray tube 8 may be the rotating cathode type as shown in FIG. 8, for example. The X-ray tube 8 shown in FIG. 8 includes a cathode (filament) 51 for discharging thermoelectrons, an anode 52 for generating X rays from the thermoelectrons discharged from the cathode 51, and a support 53 for supporting the cathode 51. In practice, the thermoelectrons discharged from the cathode 51 are converted into X rays at the anode 52 only at a low ratio, the remainder being converted into heat. To prevent damage by the heat generated at the anode 52, the X-ray tube 8 has the anode 52 constructed and fixed in an annular shape around an axis parallel to the sectional axis, the support 53 being formed annular around the axis parallel to the sectional axis, and the cathode 51 being rotatable with the support 53 about the sectional axis.

With this construction, the cathode 51 rotates with the support 53 about the sectional axis while discharges thermoelectrons, and the anode 52 fixed in the annular shape around the sectional axis receives the thermoelectrons only locally. Thus, the anode 52 may be free from damage by the heat generated thereon. The arrangement around the sectional axis reduces the force applied to the cathode 51 and support 53 as a result of rotation about the sectional axis of the X-ray tube 8 and FPD 9 combined with the inertia accompanying the rotation of support 53 and cathode 51. The burden on the X-ray tube 8 can also be reduced.

In this modification, since the cathode 51 is rotated about the sectional axis while emitting X rays, it is not necessary to rotate the X-ray tube 8 about the sectional axis as in the foregoing embodiment. The X-ray tube 8 is fixed on the scan frame 3 (FIG. 3). Thus, the X-ray tube frame 6 (FIG. 4) surrounding the X-ray tube 8 is dispensable, and the X-ray tube 8 is constructed as a housing for replacing the X-ray tube frame 6. In this modification, therefore, the cathode 51 in the X-ray tube 8 corresponds to the radiation source in this invention. The X-ray tube 8 corresponds to the radiation source housing in this invention. It will be appreciated, therefore, that the X-ray tube 8 (radiation source housing) and the cathode 51 are rotated within the fixed housing about the sectional axis.

This invention is not limited to the X-ray tube shown in FIG. 5 or the X-ray tube shown in FIG. 8 as long as a synchronous rotating scan can be carried out at high speed. For example, an X-ray tube of the electron beam control type may be employed.

The following second embodiment is a solution to the problem (II).

Second Embodiment

Like reference numerals are used to identify like parts which are the same as in the first embodiment and will not be described again.

FIG. 3 is a perspective view showing an outline of a radiographic apparatus in this embodiment. FIG. 4 is a right-hand side view of an X-ray tube frame and a flat panel detector (hereinafter called "FPD" as appropriate) frame of the radiographic apparatus in this embodiment.

In this embodiment, the scanning action of X-ray tube 8 and FPD 9 by rotation about the sectional axis is defined as "main scan", and the scanning action of X-ray tube 8 and FPD 9 by rotation about the scan center axis is defined as "auxiliary scan". Thus, the rotary drive motor 10 for rotating the X-ray tube 8 and FPD 9 about the sectional axis corresponds to the main scan rotating device. The turntable 4 for rotating the X-ray tube 8 and FPD 9 about the scan center axis corresponds to the auxiliary scan rotating device. The scan frame 3 having the turntable 4 and rotary drive motor 10 corresponds to the scan device in this invention.

According to the radiographic apparatus in this embodiment, the rotary drive motor 10 rotates the X-ray tube 8 and FPD 9 together about the sectional axis B. Thus, the X-ray tube 8 and FPD 9 are not rotated about an axis other than the sectional axis B, as distinct from the prior art. The X-ray tube 8 and FPD 9 may be rotated directly about the sectional axis. This realizes a high-speed main scan. Further, the turntable 4 is provided for rotating the X-ray tube 8 and FPD 9 together relative to the patient M about the scan center axis A which is one of axes perpendicular to the sectional axis B. With the main scan by the rotary drive motor 10 added to the auxiliary scan by the turntable 4, a three-dimensional sectional image with isotropic spatial resolution may be obtained from a reconstruction following a data collecting operation.

In this embodiment, the X-ray tube frame 6 surrounds the X-ray tube 8, the FPD frame 7 surrounds the FPD 9, and the rotary drive motor 10 rotates the X-ray tube 8 and FPD 9 together about the sectional axis B on the respective frames 6 and 7. Further, the scan frame 3 surrounds the X-ray tube 8 and FPD 9, and the turntable 4 rotates the X-ray tube 8 and FPD 9 together on the scan frame 3 about the scan center axis. More particularly, as shown in FIG. 3, the entire scan frame 3 is rotated about the scan center axis, thereby rotating the X-ray tube 8 and FPD 9 about the scan center axis, and the entire X-ray tube frame 6 and FPD frame 7 are rotated about the sectional axis, thereby rotating the X-ray tube 8 in the X-ray tube frame 6 and the FPD 9 in the FPD frame 7 about the sectional axis.

In this embodiment, the tomosynthetic angle is set to 20°, which is less than 45°. Thus, the rotation in the main scan about the sectional axis is faster than the rotation in the auxiliary scan about the scan center axis.

Where the tomosynthetic angle is $\alpha$, the range of rotation in the auxiliary scan about the scan center axis may be set to at least $\pi - 2\alpha$. Then, a three-dimensional sectional image with isotropic spatial resolution may be obtained from the set range, without setting the range of rotation in the auxiliary scan about the scan center axis to $2\pi$ (one revolution) since the rotation in the main scan also takes place.

In this embodiment, the scan center axis A of the auxiliary scan is a horizontal axis while the sectional axis B of the main scan is in a vertical plane.

By reducing the tomosynthetic angle $\alpha$, for example, the time taken for the X-ray tube 8 and FPD 9 to make one rotation about the sectional axis may be shortened. Consequently, the time taken for the X-ray tube 8 and FPD 9 to make one rotation about the sectional axis may be set to 0.1 second or less, for example. This enables a grasp of variations with time of a sectional image such as a dynamic sectional image of the heart, for example.

For example, a reduced distance between X-ray tube 8 and FPD 9 can shorten the time taken for the X-ray tube 8 and FPD 9 to make one rotation about the sectional axis. This allows the time taken for the X-ray tube 8 and FPD 9 to make a half rotation about the sectional axis to be set to 5 seconds or less. The patient M, who is an object under examination in this instance, can hold his or her breath or keep the body motionless for about 5 seconds or less. The X-ray tube 8 and FPD 9 may make a half rotation together about the scan center axis while the patient M holds his or her breath or keep still. This results in a sectional image with little slippage.

The scan frame 3 in this embodiment is channel-shaped as shown in FIG. 4. This construction provides an advantage that the patient M may undergo a photographing process without a stifling sensation as occurs in the gantry of an X-ray CT apparatus.

This invention is not limited to the foregoing embodiment, but may be modified as follows:

(1) The foregoing embodiment detects radiation, typically X rays, and obtains a sectional image from the radiation. The invention is not limited to radiation, but may employ any electromagnetic wave. For example, light may be detected to obtain a sectional image therefrom. In this case, the flat panel detector (FPD) is a light sensitive detector for generating carriers from incident light.

(2) In the foregoing embodiment, the detecting device in this invention is the flat panel detector (FPD). The detecting device is not limited to a particular type as long as it detects an electromagnetic wave. The detecting device may be an image intensifier, for example.

(3) In the foregoing embodiment, the radiation source of this invention is the X-ray tube 8 which emits X rays. The invention is not limited to the above, but may employ a device for emitting any electromagnetic wave. For example, the radiation source may emit light.

(4) In the foregoing embodiment, the frames 3, 6 and 7 are in the form of housings, the scan frame 3 being rotated about the body axis of patient M, i.e. the scan center axis, and the X-ray tube 8 and FPD 9 on the X-ray tube frame 6 and FPD frame 7 on the scan frame 3 being rotated about the sectional axis. The invention is not limited to the housings as long as the X-ray tube 8 corresponding to the radiation source in this invention and the FPD 9 corresponding to the detecting device in this invention are rotated together about the sectional axis, and are rotated together relative to the patient M about the scan center axis.

In the foregoing embodiment, the scan frame 3 is rotated about the scan center axis to rotate the X-ray tube frame 6 and the FPD frame 7 in the scan frame 3, and further the X-ray tube 8 and FPD 9 in the respective frames 6 and 7, about the scan center axis. For example, the X-ray tube frame 6 and FPD frame 7 may be provided independently of the scan frame 3 instead of being enclosed therein. These X-ray tube frame 6 and FPD frame 7 may be fixed, with only the patient M rotated about the scan center axis relative to the frames 6 and 7.

Similarly, the X-ray tube frame 6 and FPD frame 7 may be provided independently of the scan frame 3 instead of being enclosed therein, and the X-ray tube frame 6 and FPD frame 7 may be rotated, as interlocked to each other, about the scan center axis relative to the patient M. Of course, the patient M may also be rotated about the scan center axis at this time.

In the foregoing embodiment, the X-ray tube 8 and FPD 9 in the respective frames 6 and 7 are rotated about the sectional axis. In this way, the X-ray tube 8 and FPD 9 are rotated directly about the sectional axis. The frames 6 and 7 need not be in the form of housings as long as the X-ray tube 8 and FPD 9 are rotated directly about the sectional axis.

(5) In the foregoing embodiment, the X-ray tube 8 in the X-ray tube frame 6 and the FPD 9 in the FPD frame 7 are rotated about the sectional axis by rotating the respective frames 6 and 7 about the sectional axis. Instead, the frames 6 and 7 may be fixed, with the X-ray tube 8 and FPD 9 rotated in the respective frames 6 and 7 about the sectional axis.

(6) In the foregoing embodiment, the scan center axis A is a horizontal axis, and the sectional axis B is on a vertical plane. Thus, the scan center axis A extends perpendicular to the sectional axis B. It is not absolutely necessary that the two axes are precisely perpendicular to each other. The two axes may be approximately perpendicular to each other.

Figure 10:
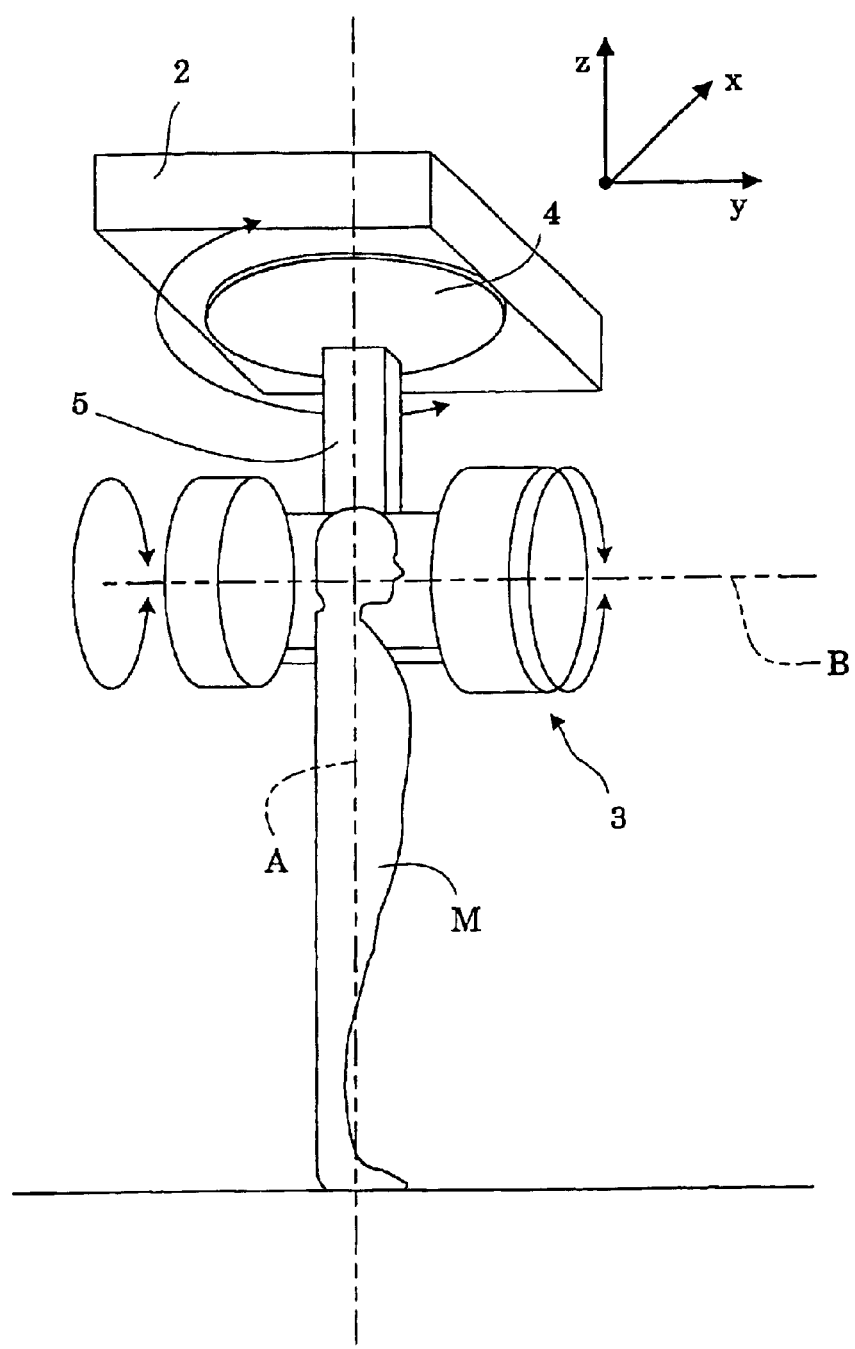
FIG. 10 is a perspective view showing an outline of a modified radiographic apparatus.
Figure 11:
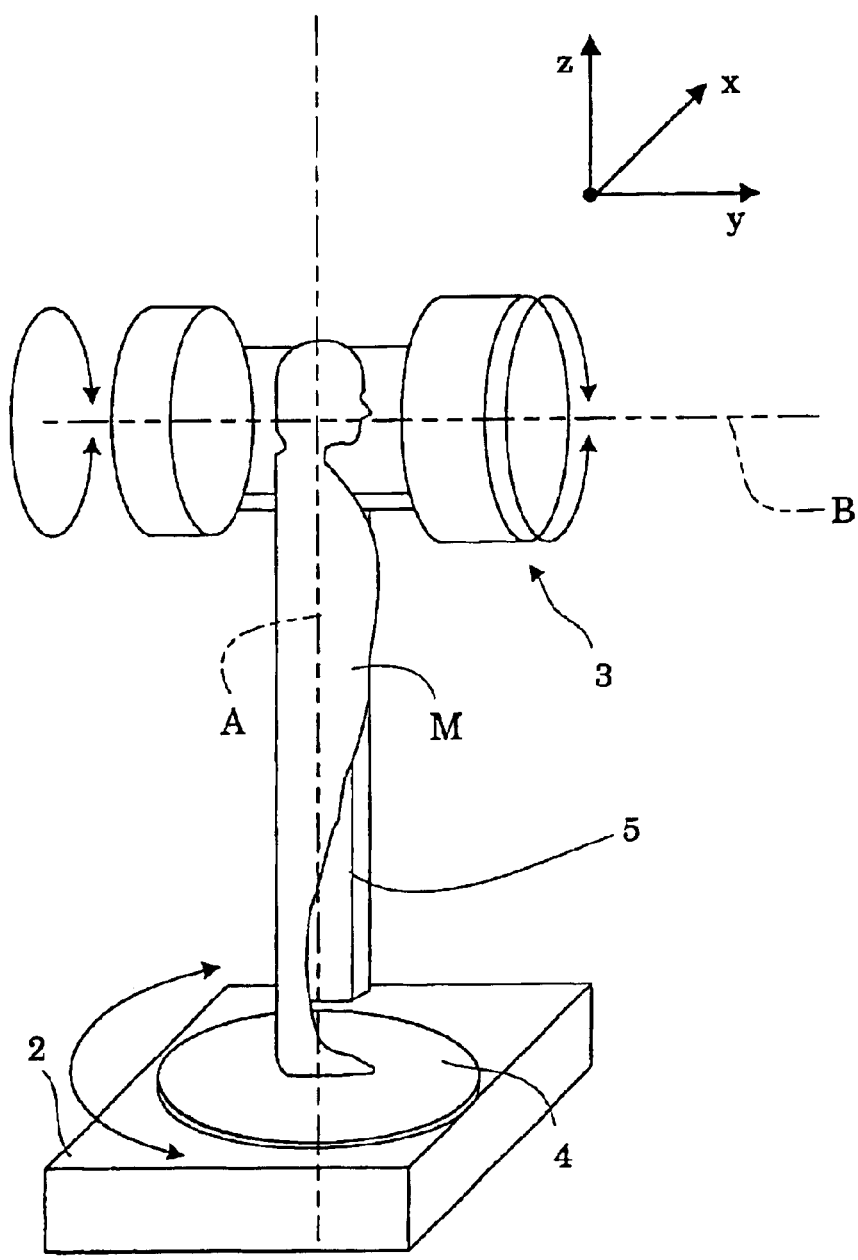
FIG. 11 is a perspective view showing an outline of another modified radiographic apparatus.

The direction of the scan center axis A of the auxiliary scan and the direction of the sectional axis B of the main scan are not limited to those in the foregoing embodiment (see FIG. 3). As shown in FIGS. 10 and 11, for example, the scan center axis A of the auxiliary scan may be a vertical axis, and the sectional axis B of the main scan a horizontal axis. FIG. 10 is a perspective view showing an outline of a modified radiographic apparatus, in which the radiation source (X-ray tube 8) and detecting device (FPD 9) are rotatable about an axis perpendicular to a ceiling surface. FIG. 11 is a perspective view showing an outline of another modified radiographic apparatus, in which the patient M is rotatable about an axis perpendicular to a floor surface. In FIGS. 10 and 11, the patient M is in standing posture, and the top board shown in FIG. 3 is not needed. Where, as shown in FIG. 11, the patient M is rotated on a turntable 4, support bars may be erected for the patient M to hold.

In FIG. 10, the base 2 is fixed to the ceiling surface, and the turntable 4 disposed on the undersurface of base 2 is rotatable about a vertical axis (scan center axis A). The scan frame 3 is thereby rotated through the support member 5 about the scan center axis relative to the ceiling surface. Consequently, the X-ray tube frame 6 and FPD frame 7 in the scan frame 3, and further the X-ray tube 8 and FPD 9 in the respective frames 6 and 7, rotate about the scan center axis relative to the ceiling surface. On the other hand, the X-ray tube 8 and FPD 9 on the respective frames 6 and 7 are rotatable together about the horizontal axis (sectional axis B).

In FIG. 11, the base 2 is fixed to the floor surface, and the turntable 4 disposed on the upper surface of base 2 is rotatable about a vertical axis (scan center axis A). With the scan frame 3 fixed, the patient M on the turntable 4 is rotated about the scan center axis relative to the floor surface. That is, the X-ray tube frame 6 and FPD frame 7 in the scan frame 3, and further the X-ray tube 8 and FPD 9 in the respective frames 6 and 7, rotate about the scan center axis relative to the floor surface. On the other hand, the X-ray tube 8 and FPD 9 on the respective frames 6 and 7 are rotatable together about the horizontal axis (sectional axis B). In the apparatus shown in FIG. 11, the scan frame 3 is fixed with the support member 5 disposed in a fixed position on the surface of the base 2 other than the turntable 4.

Apart from the modifications noted above, the scan center axis A and sectional axis B are of course not limited to the vertical plane or horizontal plane, but may extend obliquely, as long as the scan center axis A is one of axes extending substantially perpendicular to the sectional axis B.

(7-1) In the foregoing embodiment, the turntable 4 disposed on the fixed base 2 rotates the scan frame 3 through the support member 5 about the scan center axis. The construction for rotating the scan frame 3 is not limited to such.

For example, a radiographic apparatus may have a scan frame, a support member for supporting the scan frame, and a transmission device disposed between the scan frame and support member for rotating the scan frame about the scan center axis (auxiliary scan rotation).

Figure 12A:
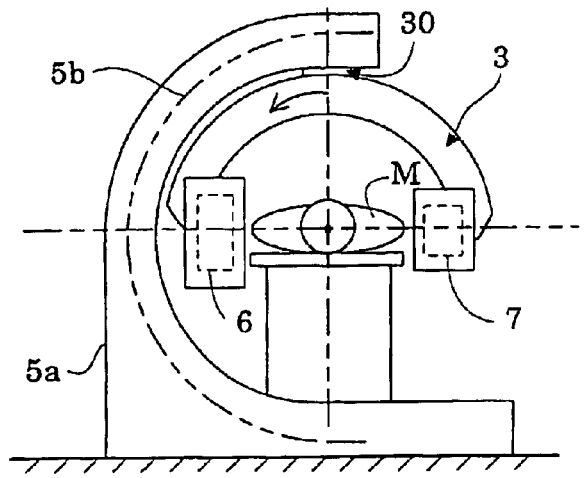
FIG. 12A is a schematic view of a modified radiographic apparatus.
Figure 12B:
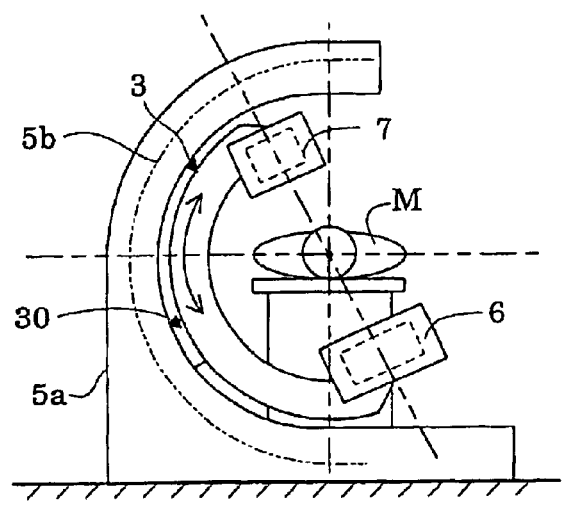
FIG. 12B is a schematic view of the modified radiographic apparatus.
Figure 12C:
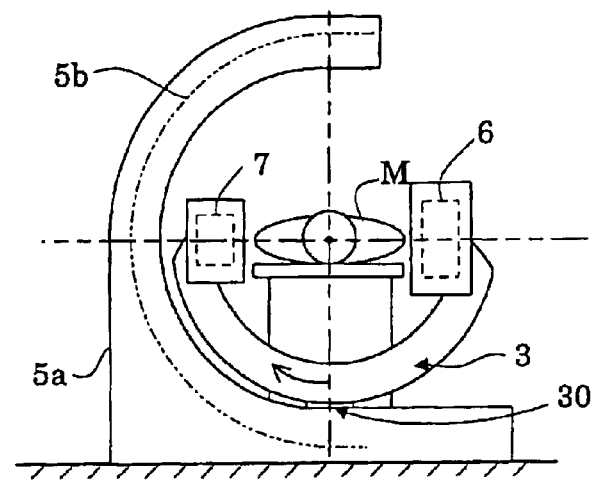
FIG. 12C is a schematic view of the modified radiographic apparatus.

This construction will particularly be described with reference to FIGS. 12A–12C and 13. FIGS. 12A–12C are schematic views of this modified radiographic apparatus, showing positions of the scan frame 3 at different points of time. The scan frame 3 has a C arm configuration. A support member 5a holding this scan frame 3 is fixedly mounted on a floor surface. The support member 5a has an arcuate portion with an inner peripheral surface thereof holding the scan frame 3 for making an auxiliary scan rotation.

Figure 13:
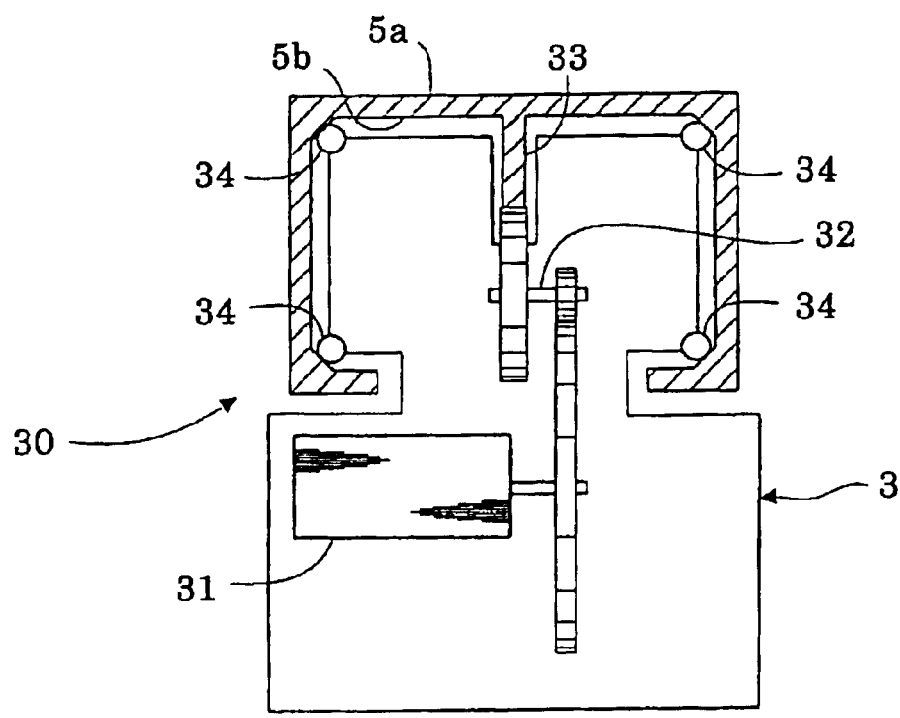
FIG. 13 is a view in vertical section of a connection between a scan frame and a support member.

FIG. 13 is a view in vertical section of a connection 30 between the scan frame 3 and support member 5a. The support member 5a has, formed in the inner peripheral surface of the arcuate portion thereof, a guide groove 5b for holding and allowing the auxiliary scan rotation of the scan frame 3, and a bearing 33 for auxiliary scan rotation. On the other hand, the scan frame 3 has, arranged therein, a motor 31 for auxiliary scan rotation, an auxiliary scan rotary shaft 32, and gears. The motor 31 for auxiliary scan rotation and the auxiliary scan rotary shaft 32 are connected through gears. The auxiliary scan rotary shaft 32 and the bearing 33 for auxiliary scan rotation are also connected through gears. These components constitute the above transmission device. The transmission device connects the scan frame 3 and support member 5a, and causes the scan frame 3 to make the auxiliary scan rotation along the guide groove 5b.

The above support member 5a corresponds to the scan housing support member in this invention. The transmission device corresponds to the feed mechanism in this invention.

The guide groove 5b is formed to enable a rotation through about 180° of the scan frame 3. The scan frame 3 makes the auxiliary scan rotation through a reciprocating motion as shown in FIGS. 12A, 12B and 12C. Furthermore, bearing elements 34 are arranged in locations where the scan frame 3 contacts the guide groove 5b of support member 5a. These elements 34 allow the scan frame 3 to rotate smoothly.

With the above construction, the base 2 and turntable 4 are omitted to reduce a floor area for installing the whole radiographic apparatus.

When the scan frame 3 is in the position shown in FIG. 12C which is home position for performing an IVR procedure, for example, an upper area is open to give the patient M a feeling of openness.

In this modification, the motor 31 for auxiliary scan rotation and so on of the transmission device are arranged in the scan frame 3. These components may be arranged in the support member 5a. In this modification, the guide groove 5b is formed to enable a rotation through about 180° of the scan frame 3. The range of the guide groove is not limited to the above as long as a three-dimensional sectional image with isotropic spatial resolution is obtained with the main scan taken into consideration.

(7-2) In the above modification, the support member 5a has an arcuate portion. The support member need not have such an arcuate portion as long as it allows the scan frame 3 to make an auxiliary scan rotation.

Figure 14A:
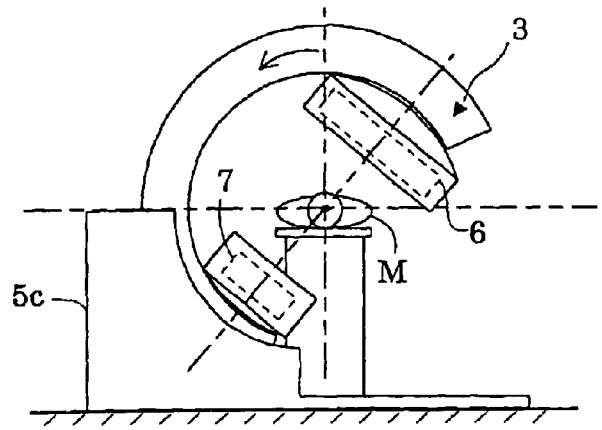
FIG. 14A is a schematic view of a modified radiographic apparatus.
Figure 14B:
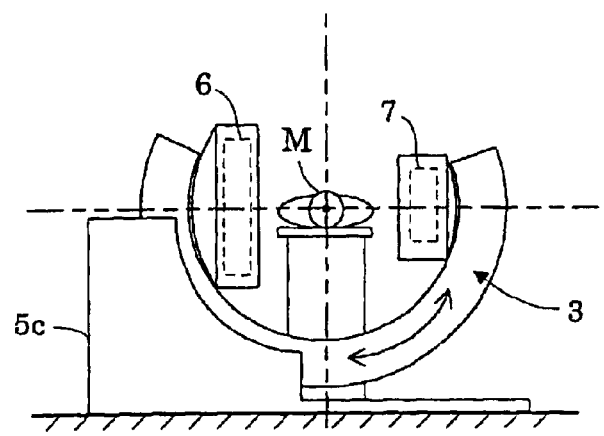
FIG. 14B is a schematic view of the modified radiographic apparatus.
Figure 14C:
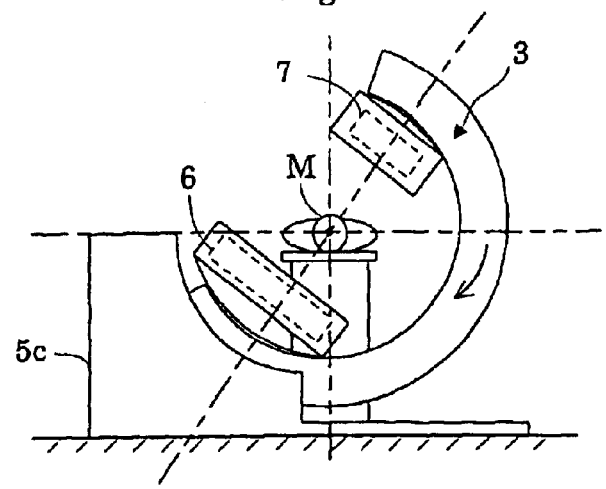
FIG. 14C is a schematic view of the modified radiographic apparatus.

This aspect will particularly be described with reference to FIGS. 14A–14C and 15. FIGS. 14A–14C are schematic views of this modified radiographic apparatus, showing positions of the scan frame 3 at different points of time. The scan frame 3 in this modification also has a C arm configuration. A support member 5c holding the scan frame 3 is fixedly mounted on a floor surface.

Figure 15:
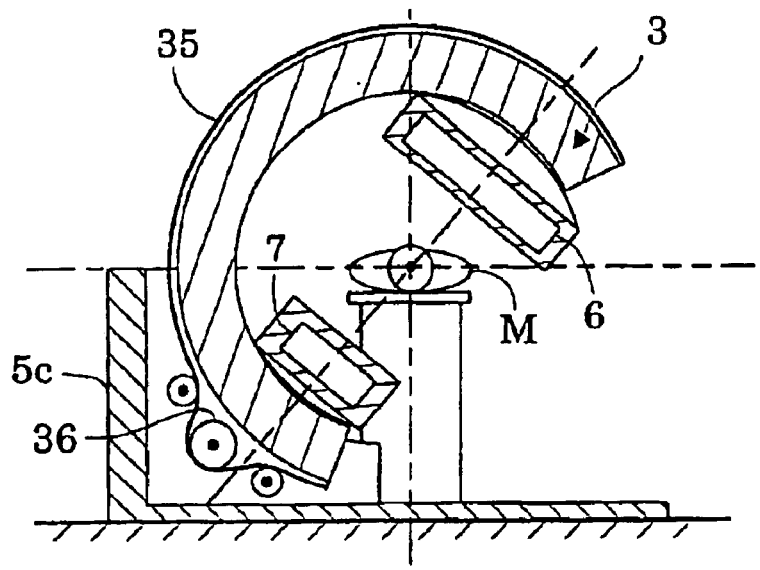
FIG. 15 is a view in vertical section of the modified radiographic apparatus.

FIG. 15 is a view in vertical section of this modified radiographic apparatus. The scan frame 3 has an auxiliary scanning belt 35 extending along an arcuate outer periphery thereof. The support member 5c has rollers 36 for feeding the auxiliary scanning belt 35, and a drive device, not shown, for rotating the rollers 36. The auxiliary scanning belt 35, rollers 36 and drive device constitute a transmission device for causing the scan frame 3 to make a 180° auxiliary scan rotation through a reciprocating motion as shown in FIGS. 14A–14C.

The above support member 5c corresponds to the scan housing support member in this invention. The transmission device including the auxiliary scanning belt 35, rollers 36 and drive device corresponds to the feed mechanism in this invention.

With the above construction, the whole radiographic apparatus requires a reduced floor area for installation. The support member 5c holding the scan frame 3 may be reduced in size.

When the scan frame 3 is in the position shown in FIG. 14B which is home position for performing an IVR procedure, an upper area is open to give the patient M a feeling of openness.

(8) The foregoing embodiment may generate X rays at predetermined times based on the periodic motion of the patient's heart.

Figure 16:
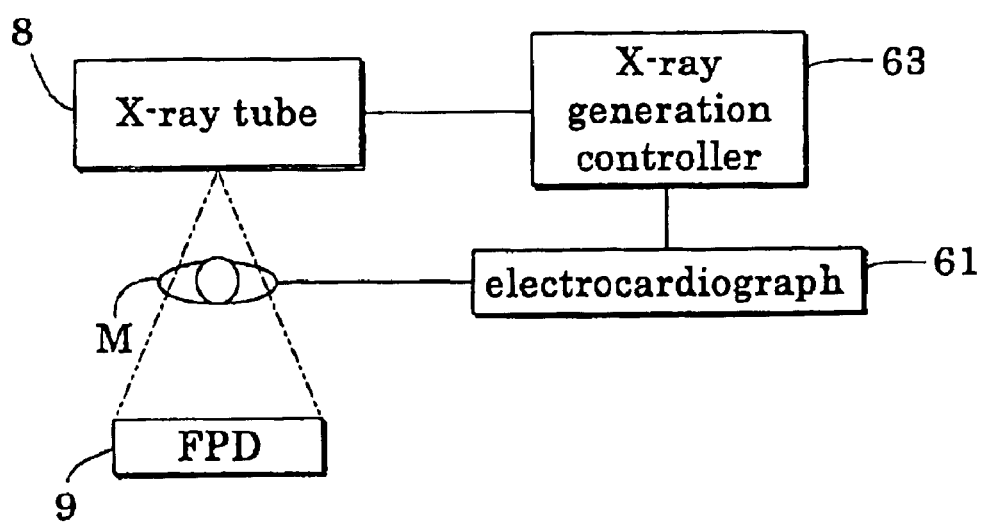
FIG. 16 is a block diagram of a modified radiographic apparatus.
Figure 17A:
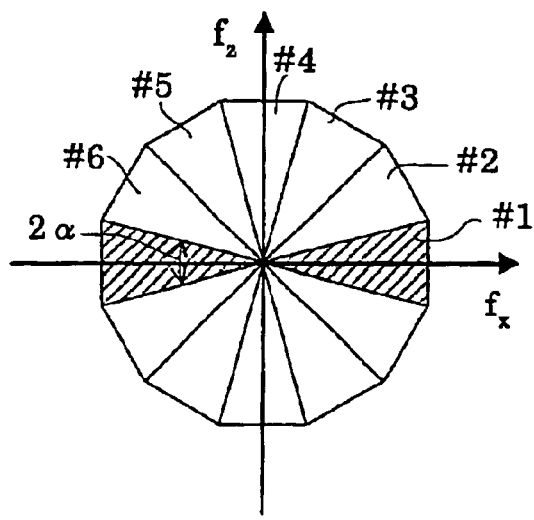
FIG. 17A is a view showing a collected data distribution in Fourier space for illustrating a three-dimensional sectional image collection with isotropic resolution from a heart region.

This aspect will particularly be described with reference to FIGS. 16, 17A and 17B. FIG. 16 is a block diagram of a radiographic apparatus according to this modification. An X-ray tube 8 is disposed above the patient M for emitting X rays. An FPD 9 is disposed below the patient M for detecting the X rays. The X rays are emitted in a cone beam shape to the patient M, and transmitted through the patient M to impinge on the FPD 9.

Further, an electrocardiograph 61 is attached to the patient M for measuring the heartbeat of the patient M. The electrocardiograph 61 is electrically connected to an X-ray generation controller 63 that controls X-ray emission from the X-ray tube 8.

The electrocardiograph 61 corresponds to the measuring device in this invention for detecting biosignals. The X-ray generation controller 63 corresponds to the radiation source control device in this invention.

The radiographic apparatus having the above construction operates as follows. As shown in FIG. 17B, the motion of the heart of patient M is detected by the electrocardiograph 61 as an electrocardiographic (ECG) waveform. This electrocardiographic (ECG) waveform is inputted to the X-ray generation controller 63. The X-ray generation controller 63 determines from the electrocardio-graphic (ECG) waveform that the heart becomes a predetermined state, and controls the X-ray tube 8 to emit X rays synchronously with this timing. The predetermined state is the systole or diastole, depending on which state is to be reflected on the three-dimensional sectional images acquired. Under control of the X-ray generation controller 63, the X-ray tube 8 emits X rays to the patient M after a delay time t. X rays transmitted through the patient M are detected and collected as projection data by the FPD 9. In this way, projection data is collected only when the heart is in the same state.

A relationship between the main scan and the collection of projection data will be described in greater detail. Data collection is performed in synchronism with the electrocardiographic (ECG) waveform as shown in FIG. 17B, in order to obtain three-dimensional sectional images free from motion artifacts of the heart. As shown in hatched (oblique lines) portions in FIG. 17A, a Fourier space distribution of data obtained from one main scan rotation is a range of 30° (=2×α). It will be seen from FIGS. 17A and 17B that six main scan data collections may be carried out each corresponding to 30° of the auxiliary scan, to collect data for filling the entire Fourier space, i.e. to collect data for a three-dimensional sectional image with isotropic spatial resolution.

Figure 17B:
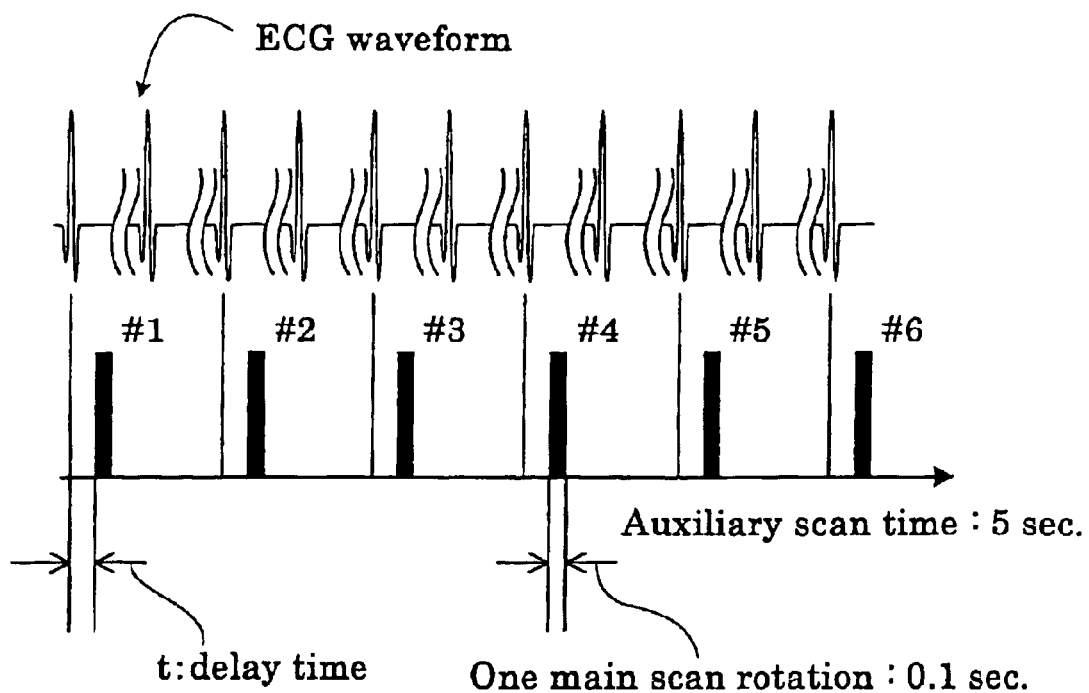
FIG. 17B is a data collection timing chart for illustrating the three-dimensional sectional image collection with isotropic resolution from the heart region.

More particularly, as shown in the timing chart of FIG. 17B also, a transmitted X-ray image collection of the patient is performed during one main scan rotation, which is a continuous high-speed rotation, at a predetermined delay time after the a wave of ECG. This collecting operation is carried out a total of six times each synchronized to ECG of every 30°. In practice, the main scan rotation takes place continuously for five seconds of the auxiliary scan, instead of being limited to the times (0.1 second) represented by the black portions in FIG. 17B. The black portions represent times (0.1 second) when electromagnetic waves (X rays in this case) are emitted from the radiation source.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus comprising:
    a radiation source for emitting an electromagnetic wave to an object under examination;
    detecting means for detecting said electromagnetic wave emitted to and transmitted through said object; and
    scan means for moving said radiation source and said detecting means together for scanning action;
    a three-dimensional sectional image being obtained from a group of projection data detected in varied positions of said detecting means moved by said scan means;
    wherein said radiation source and said detecting means are arranged such that a radiation axis linking said radiation source and said detecting means is inclined at a predetermined angle relative to a sectional axis passing through a site of interest of said object; and
    said scan means includes a radiation source housing for surrounding said radiation source, a detecting means housing for surrounding said detecting means, and rotating means for rotating said radiation source and said detecting means in the respective housings together about said sectional axis.

2. A radiographic apparatus as defined in claim 1, wherein said radiation source housing and said detecting means housing are connected to a rotary shaft connected to said rotating means, said rotary shaft being disposed at an end of each of said housings.

3. A radiographic apparatus as defined in claim 1, wherein said detecting means is a flat panel detector having a plurality of gate lines switchable on and off for taking in said electromagnetic wave transmitted, and a plurality of read lines extending perpendicular to said gate lines for reading said projection data, said flat panel detector being disposed such that each of said read lines extends along a projection axis formed by said sectional axis projected on a detecting plane of said flat panel detector.

4. A radiographic apparatus as defined in claim 3, wherein said gate lines are turned on simultaneously to take in said electromagnetic wave in positions corresponding to said gate lines simultaneously as electric charges, said electric charges taken in being read as said projection data through said read lines, a lowpass filtering being effected on said projection data by turning on said gate lines simultaneously.

5. A radiographic apparatus as defined in claim 1, said scan means is arranged such that said rotating means rotates said radiation source and said detecting means together to make one rotation about said sectional axis in 0.1 second at most.

6. A radiographic apparatus as defined in claim 1, wherein said radiation source is an X-ray tube for emitting X rays, said X-ray tube being a rotating anode X-ray tube including a cathode for discharging thermoelectrons, an anode for generating X rays upon collision with accelerated thermoelectrons from said cathode, and an anode rotating shaft for rotating said anode, said X-ray tube being constructed and arranged so that said anode rotating shaft is parallel to said sectional axis.

7. A radiographic apparatus as defined in claim 1, wherein said radiation source is an X-ray tube for emitting X rays, said X-ray tube being a rotating cathode X-ray tube including a cathode for discharging thermoelectrons, an anode for generating X rays upon collision with accelerated thermoelectrons from said cathode, and a support for supporting said cathode, said anode being shaped annular and fixed around an axis parallel to said sectional axis, said support being shaped annular around said axis parallel to said sectional axis, said X-ray tube being arranged so that said cathode is rotatable with said support about said axis parallel to said sectional axis.

8. A radiographic apparatus comprising:

a radiation source for emitting an electromagnetic wave to an object under examination;

detecting means for detecting said electromagnetic wave emitted to and transmitted through said object;

scan means for moving said radiation source and said detecting means together for scanning action; and an image processor for obtaining a three-dimensional sectional image from a group of projection data detected in varied positions of said detecting means moved by said scan means;

wherein said radiation source and said detecting means are arranged such that a radiation axis linking said radiation source and said detecting means is inclined at a predetermined angle relative to a sectional axis passing through a site of interest of said object; and said scan means includes main scan rotating means for rotating said radiation source and said detecting means together about said sectional axis, and auxiliary scan rotating means for rotating said radiation source and said detecting means together relative to said object about a scan center axis which is one of axes extending substantially perpendicular to said sectional axis.

9. A radiographic apparatus as defined in claim 8, wherein said scan means includes a radiation source housing for surrounding said radiation source, and a detecting means housing for surrounding said detecting means, said main scan rotating means rotating said radiation source and said detecting means in the respective housings together about said sectional axis.

10. A radiographic apparatus as defined in claim 8, wherein said scan means includes a scan housing for surrounding said radiation source and said detecting means, said auxiliary scan rotating means rotating said radiation source and said detecting means in said scan housing together about said scan center axis.

11. A radiographic apparatus as defined in claim 10, wherein said auxiliary scan rotating means includes a scan housing support member for holding said scan housing, and a feed mechanism between said scan housing support member and said scan housing for rotating said scan housing.

12. A radiographic apparatus as defined in claim 8, wherein a main scan rotation about said sectional axis is faster than an auxiliary scan rotation about said scan center axis.

13. A radiographic apparatus as defined in claim 8, wherein a range of auxiliary scan rotation about said scan center axis is set to at least $\pi-2\alpha$, where $\alpha$ is a tomosynthetic angle between said sectional axis and said radiation axis linking said radiation source and said detecting means.

14. A radiographic apparatus as defined in claim 8, wherein said scan center axis of said auxiliary scan is a horizontal axis, and said sectional axis of said main scan is a vertical axis.

15. A radiographic apparatus as defined in claim 8, wherein said scan center axis of said auxiliary scan is a vertical axis, and said sectional axis of said main scan is a horizontal axis.

16. A radiographic apparatus as defined in claim 15, wherein said auxiliary scan rotating means is arranged to rotate said radiation source and said detecting means together about said vertical axis relative to a ceiling surface.

17. A radiographic apparatus as defined in claim 15, wherein said auxiliary scan rotating means is arranged to rotate said object about said vertical axis relative to a floor surface.

18. A radiographic apparatus as defined in claim 8, wherein said scan means is arranged such that said main scan rotating means causes said radiation source and said detecting means to make one rotation about said sectional axis in at most 0.1 second.

19. A radiographic apparatus as defined in claim 8, wherein said scan means is arranged such that said auxiliary scan rotating means causes said radiation source and said detecting means to make a half rotation about said scan center axis in at most 5 seconds.

20. A radiographic apparatus as defined in claim 8, further comprising measuring means for detecting biosignals from said object, and radiation source control means for controlling said radiation source to emit the electromagnetic wave to said object synchronously with predetermined times in a periodic motion detected by said measuring means.

* * * * *